US012640260B2

(12) United States Patent     (10) Patent No.:   US 12,640,260 B2
Azizian et al.                (45) Date of Patent:     May 26, 2026

(54) BEACON-BASED SYSTEMS AND METHODS FOR GENERATING MEDICAL FACILITY METRICS

(71) Applicant: Intuitive Surgical Operations, Inc., Sunnyvale, CA (US)

(72) Inventors: Mahdi Azizian, San Jose, CA (US); Christopher R. Burns, San Jose, CA (US); Boris Foelsch, Palo Alto, CA (US); Liron Leist, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 72 days.

(21) Appl. No.: 18/651,318

(22) Filed: Apr. 30, 2024

(65) Prior Publication Data

US 2024/0282436 A1     Aug. 22, 2024

Related U.S. Application Data

(62) Division of application No. 17/103,661, filed on Nov. 24, 2020, now Pat. No. 12,027,257.

(Continued)

(51) Int. Cl.
| | |
|---|---|
| *G16H 40/20* | (2018.01) |
| *A61B 34/00* | (2016.01) |
| *A61B 90/98* | (2016.01) |
| *G06K 7/10* | (2006.01) |
| *G06K 7/14* | (2006.01) |

(Continued)

(52) U.S. Cl.
CPC ............. *G16H 40/20* (2018.01); *A61B 34/25* (2016.02); *A61B 90/98* (2016.02); *G16H 40/67* (2018.01); *H04W 4/38* (2018.02);

*H04W 8/005* (2013.01); *G06K 7/10297* (2013.01); *G06K 7/1417* (2013.01); *G16H 15/00* (2018.01);

(Continued)

(58) Field of Classification Search
CPC ........ G16H 40/20; G16H 80/00; G16H 40/67; G16H 20/40; G16H 15/00; A61B 34/25; A61B 90/98; H04W 8/005
See application file for complete search history.

(56) References Cited

U.S. PATENT DOCUMENTS

| | | | |
|---|---|---|---|
| 2013/0166256 A1* | 6/2013 | Wirx-Speetjens | ...... G06F 30/00 |
| | | | 703/1 |
| 2014/0297327 A1 | 10/2014 | Heil et al. | |

(Continued)

OTHER PUBLICATIONS

Reiley et al., Review of methods for objective surgical skill evaluation, 25 Surgical Endoscopy 356-366 (Year: 2011).*

(Continued)

*Primary Examiner* — Jordan L Jackson

(57) ABSTRACT

A beacon-based metrics system tracks, based on medical session data logged by a computer-assisted surgical system, events associated with the computer-assisted surgical system; determines that a user device that is not communicatively paired with the computer-assisted surgical system detects a beacon associated with the computer-assisted surgical system; and generates medical facility metrics data representative of the tracked events. Generating the medical facility metrics data includes identifying a set of tracked events that occur during a time period in which the user device detects the beacon and associating information associated with the user device with the set of tracked events.

20 Claims, 13 Drawing Sheets

900

Related U.S. Application Data

(60) Provisional application No. 62/940,789, filed on Nov. 26, 2019.

(51) Int. Cl.

| | |
|---|---|
| *G16H 15/00* | (2018.01) |
| *G16H 20/40* | (2018.01) |
| *G16H 40/67* | (2018.01) |
| *G16H 70/20* | (2018.01) |
| *G16H 80/00* | (2018.01) |
| *H04W 4/38* | (2018.01) |
| *H04W 8/00* | (2009.01) |

(52) U.S. Cl.
CPC ............. *G16H 20/40* (2018.01); *G16H 70/20* (2018.01); *G16H 80/00* (2018.01)

(56) References Cited

U.S. PATENT DOCUMENTS

| | | | |
|---|---|---|---|
| 2016/0174022 A1 | 6/2016 | Nhu | |
| 2017/0214788 A1* | 7/2017 | Way | H04L 51/04 |
| 2019/0053007 A1 | 2/2019 | Theurer et al. | |
| 2019/0082298 A1* | 3/2019 | Good | H04W 4/80 |
| 2019/0201136 A1 | 7/2019 | Shelton, IV et al. | |
| 2019/0327161 A1 | 10/2019 | Cannell et al. | |
| 2020/0203010 A1 | 6/2020 | Durlach et al. | |
| 2021/0158947 A1 | 5/2021 | Azizian et al. | |

OTHER PUBLICATIONS

Lopez et al., LOBIN: E-Textile and Wireless-Sensor-Network Based Platform for Healthcare Monitoring in Future Hospital Environments, 14(6) IEEE Transactions on Information Tech in Biomedicine (Nov. 6, 2010) (Year: 2010).*

Jiang, L., et al., "Integrated UWB and GPS Location Sensing System in Hospital Environment," IEEE Conference on Industrial Electronics and Applications (ICIEA), 2010, pp. 286-289.

Lopez, G., et al., "LOBIN: E-textile and Wireless-Sensor-Network Based Platform for Healthcare Monitoring in Future Hospital Environments," IEEE Transactions on Information Technology in Biomedicine, 2010, vol. 14(6), pp. 1446-1458.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

200

Medical Facility
202

Predefined Area
204

Medical System
206

214

212

208

210

300

400

500

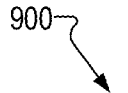
900
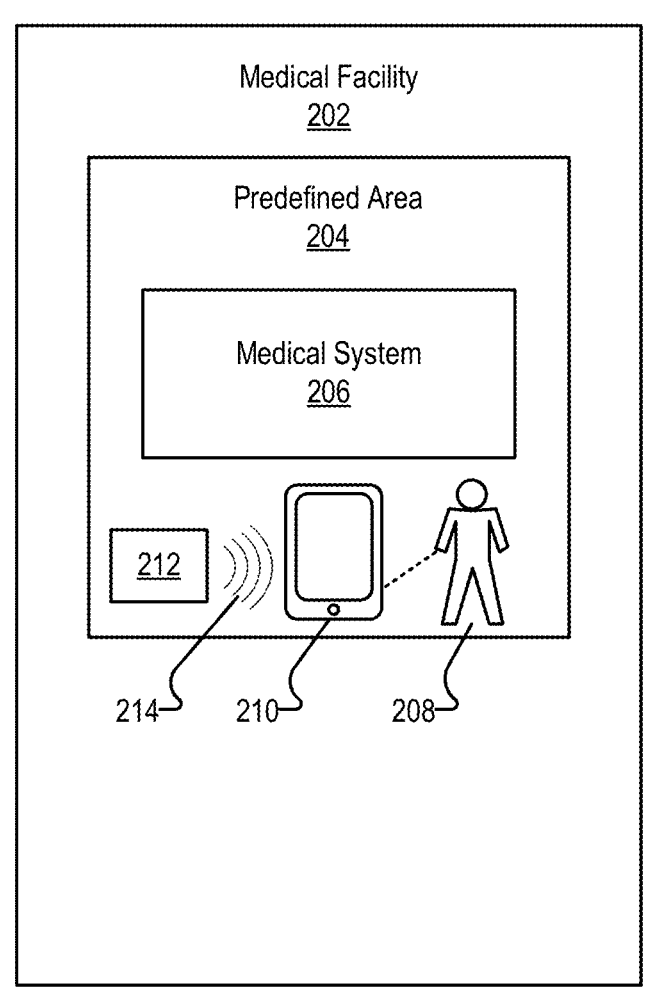
Fig. 9

| Event | Timestamp | User Device ID | User ID | Location ID | Medical System ID | Surgical Session ID |
|---|---|---|---|---|---|---|
| | 1004 | 1006 | 1008 | 1010 | 1012 | 1014 |
| Beacon01_Detected | 08:00:53 | 1234 | | RM202 | | |
| User_Login | 08:00:53 | 1234 | NURSE001 | RM202 | | |
| Open_Patient_Chart | 08:01:22 | 1234 | NURSE001 | RM202 | | |
| Input_Status | 08:03:43 | 1234 | NURSE001 | RM202 | | |
| No_Beacon | 08:07:22 | 1234 | NURSE001 | | | |
| Beacon02_Detected | 08:28:12 | 5678 | SURG023 | OR003 | DV020 | PATIENT_A |
| Targeting_Complete | 08:34:05 | 5678 | SURG023 | OR003 | DV020 | PATIENT_A |
| Adjust_Arm | 08:41:27 | 5678 | SURG023 | OR003 | DV020 | PATIENT_A |
| Arm_Collision | 08:41:32 | 5678 | SURG023 | OR003 | DV020 | PATIENT_A |
| No_Beacon | 09:22:07 | 5678 | SURG023 | | | |

1002

1000

1200

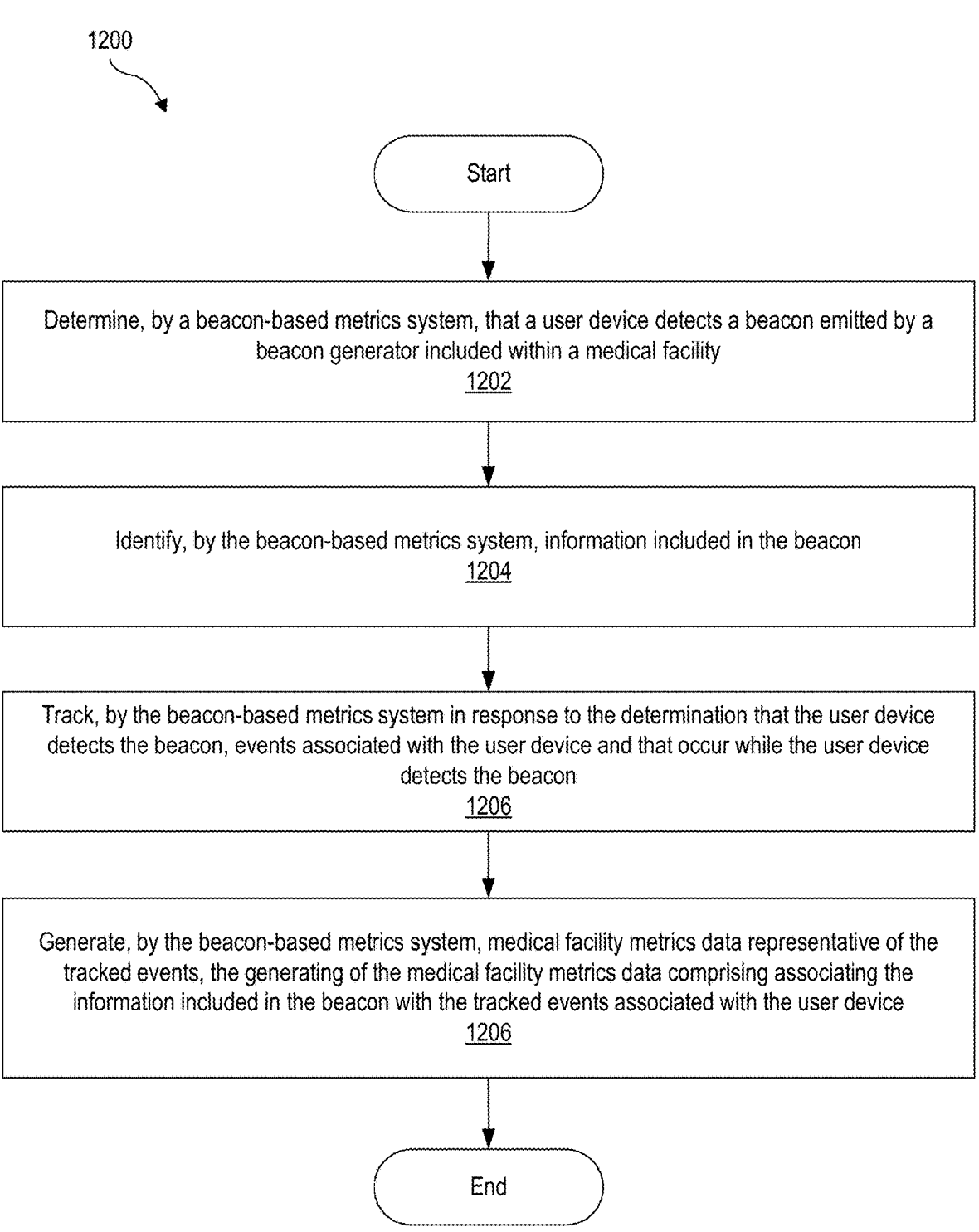

Start

Determine, by a beacon-based metrics system, that a user device detects a beacon emitted by a beacon generator included within a medical facility
1202

Identify, by the beacon-based metrics system, information included in the beacon
1204

Track, by the beacon-based metrics system in response to the determination that the user device detects the beacon, events associated with the user device and that occur while the user device detects the beacon
1206

Generate, by the beacon-based metrics system, medical facility metrics data representative of the tracked events, the generating of the medical facility metrics data comprising associating the information included in the beacon with the tracked events associated with the user device
1206

End

Fig. 12

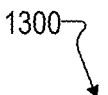
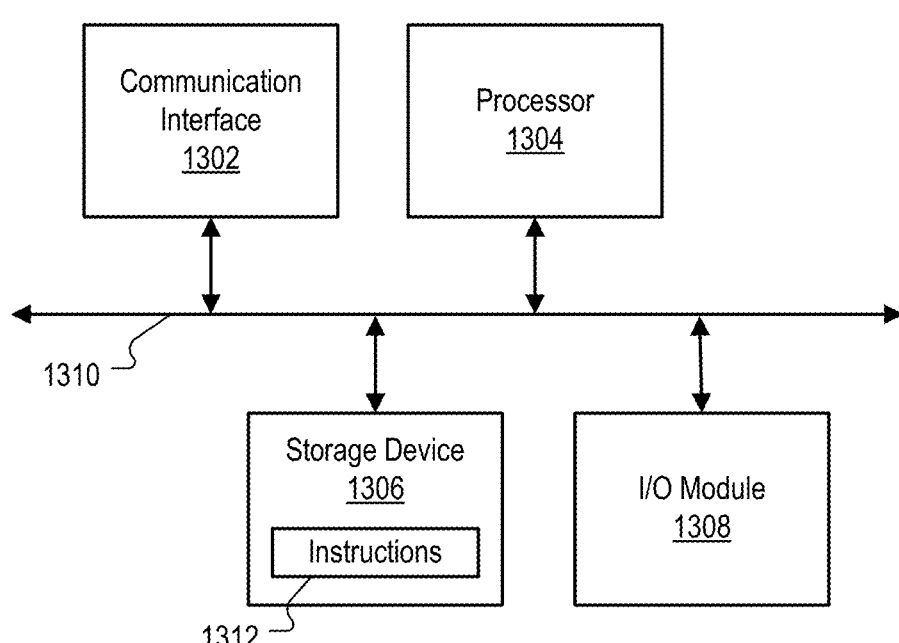
Fig. 13

BEACON-BASED SYSTEMS AND METHODS FOR GENERATING MEDICAL FACILITY METRICS

RELATED APPLICATIONS

The present application is a divisional of U.S. patent application Ser. No. 17/103,661, filed Nov. 24, 2020, which claims priority to U.S. Provisional Patent Application No. 62/940,789, filed Nov. 26, 2019, each of which are hereby incorporated by reference in their entirety.

BACKGROUND INFORMATION

In a medical facility (e.g., a hospital, a nursing home, etc.), medical personnel may diagnose, treat, and/or assist patients. In some medical facilities the actions of the medical personnel may be tracked to measure the efficiency with which medical personnel perform various tasks. However, medical personnel are frequently moving throughout the medical facility and performing many different tasks. Accordingly, it is difficult to track the medical personnel and the specific actions they perform. Manual efforts to track actions of medical personnel and measure the efficiency with which they perform various tasks may distract medical personnel from other more important tasks and undesirably decrease the efficiency of the medical personnel and of the medical facility.

SUMMARY

The following description presents a simplified summary of one or more aspects of the methods and systems described herein in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects of the methods and systems described herein in a simplified form as a prelude to the more detailed description that is presented below.

An exemplary system may comprise a memory storing instructions and a processor communicatively coupled to the memory and configured to execute the instructions to track events associated with a user device located within a medical facility, determine that the user device detects a beacon emitted by a beacon generator located within the medical facility, identify information included in the beacon, and generate medical facility metrics data representative of the tracked events, the generating of the medical facility metrics data comprising identifying a set of tracked events that occur during a time period in which the user device detects the beacon and associating the information included in the beacon with the set of tracked events.

Another exemplary system may comprise a memory storing instructions and a processor communicatively coupled to the memory and configured to execute the instructions to determine that a user device detects a beacon emitted by a beacon generator included within a medical facility, identify information included in the beacon, track, in response to the determination that the user device detects the beacon, events associated with the user device and that occur while the user device detects the beacon, and generate medical facility metrics data representative of the tracked events, the generating of the medical facility metrics data comprising associating the information included in the beacon with the tracked events associated with the user device.

An exemplary method may comprise tracking, by a beacon-based metrics system, events associated with a user device located within a medical facility; determining, by the beacon-based metrics system, that the user device detects a beacon emitted by a beacon generator located within the medical facility; identifying, by the beacon-based metrics system, information included in the beacon; and generating, by the beacon-based metrics system, medical facility metrics data representative of the tracked events, the generating of the medical facility metrics data comprising identifying a set of tracked events that occur during a time period in which the user device detects the beacon and associating the information included in the beacon with the set of tracked events.

Another exemplary method may comprise determining, by a beacon-based metrics system, that a user device detects a beacon emitted by a beacon generator included within a medical facility; identifying, by the beacon-based metrics system, information included in the beacon; tracking, by the beacon-based metrics system in response to the determination that the user device detects the beacon, events associated with the user device and that occur while the user device detects the beacon; and generating, by the beacon-based metrics system, medical facility metrics data representative of the tracked events, the generating of the medical facility metrics data comprising associating the information included in the beacon with the tracked events associated with the user device.

An exemplary non-transitory computer-readable medium stores instructions that, when executed, direct at least one processor of a computing device to track events associated with a user device located within a medical facility, determine that the user device detects a beacon emitted by a beacon generator located within the medical facility, identify information included in the beacon, and generate medical facility metrics data representative of the tracked events, the generating of the medical facility metrics data comprising identifying a set of tracked events that occur during a time period in which the user device detects the beacon and associating the information included in the beacon with the set of tracked events.

Another exemplary non-transitory computer-readable medium stores instructions that, when executed, direct at least one processor of a computing device to determine that a user device detects a beacon emitted by a beacon generator included within a medical facility; identify information included in the beacon; track, in response to the determination that the user device detects the beacon, events associated with the user device and that occur while the user device detects the beacon; and generate medical facility metrics data representative of the tracked events, the generating of the medical facility metrics data comprising associating the information included in the beacon with the tracked events associated with the user device.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 9 illustrates another exemplary configuration of a medical facility including a beacon generator located within a predefined area according to principles described herein.

FIG. 12 illustrates another exemplary method according to principles described herein.

FIG. 13 illustrates an exemplary computing device according to principles described herein.

DETAILED DESCRIPTION

Figure 1:
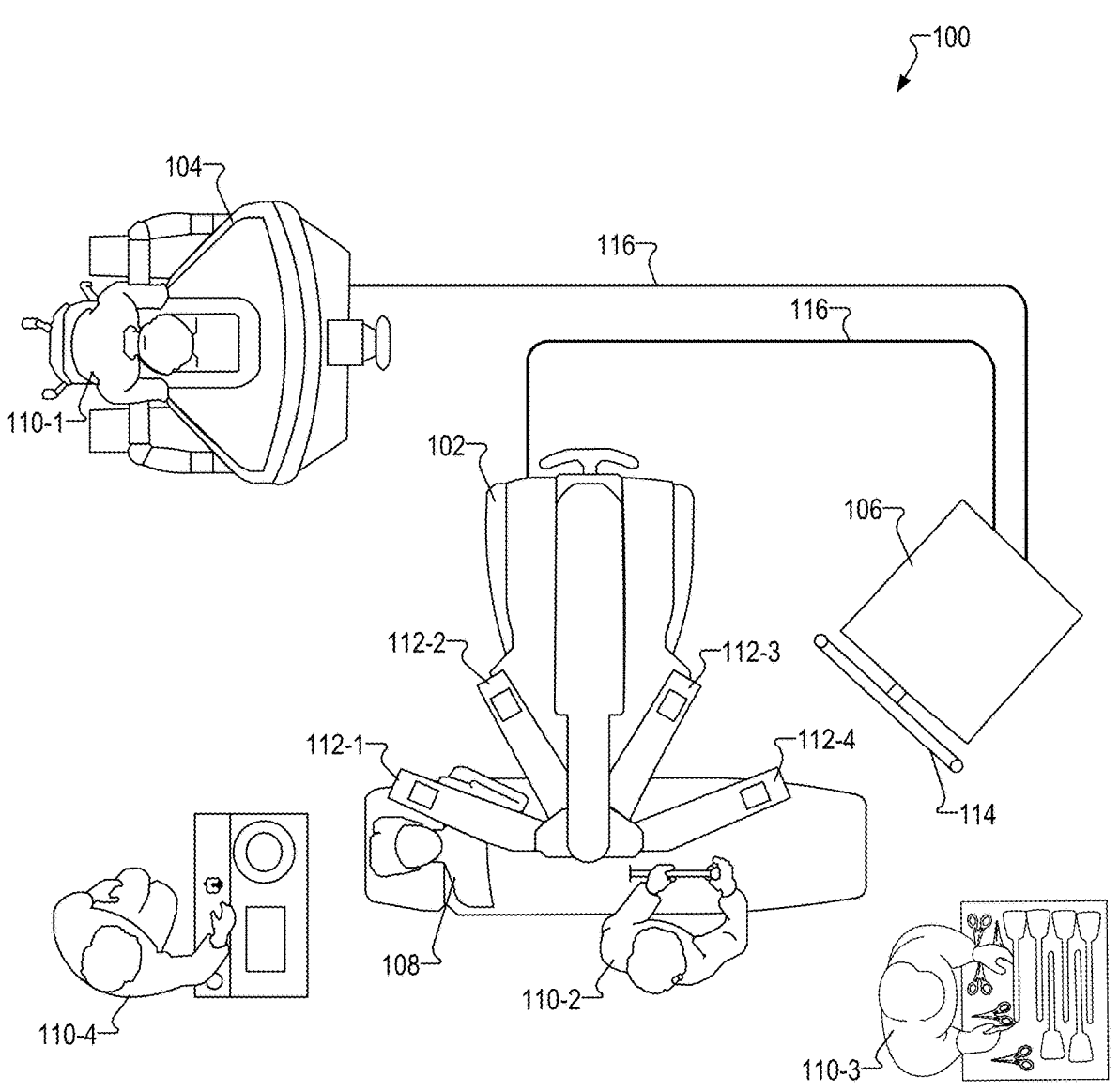
FIG. 1 illustrates an exemplary computer-assisted surgical system according to principles described herein

Beacon-based metrics systems and methods are described herein. As will be described below in more detail, a beacon-based metrics system may track events associated with a user device located within a medical facility. The beacon-based metrics system may determine that the user device detects a beacon (e.g., an ultrasonic beacon) emitted by a beacon generator located within the medical facility and identify information included in the beacon. The beacon-based metrics system may generate medical facility metrics data representative of the tracked events, such as by identifying a set of tracked events that occur during a time period in which the user device detects the beacon and associating the information included in the beacon with the set of tracked events.

In some examples, a beacon-based metrics system may determine that a user device detects a beacon emitted by a beacon generator included within a medical facility and may identify information included in the beacon. In response to the determination that the user device detects the beacon, the beacon-based metrics system may track events associated with the user device and that occur while the user device detects the beacon. The beacon-based metrics system may generate medical facility metrics data representative of the tracked events, such as by associating the information included in the beacon with the tracked events associated with the user device.

The tracked events may include, for example, detection by the user device of a beacon and/or user interactions with the user device. In some examples, the tracked events may also include user interactions with a medical system by way of the user device and/or operations of the medical system performed in response to the user interactions with the user device. For example, when the user device is communicatively paired with the medical system, a user of the user device may gain access, by way of the user device, to one or more functional features associated with the medical system. The functional features may allow the user to exchange data and content (e.g., an endoscopic video stream) with the medical system, control one or more features or settings of the medical system, view information about a medical procedure performed with the medical system (e.g., patient information, surgical team information, etc.), and/or communicate (by way of other mobile devices) with other medical personnel assisting with the medical procedure.

The information included in the beacon may include, for example, information identifying a particular location (e.g., an operating room, a patient room, an equipment room, a location near a particular component of a medical system, etc.) in which the beacon generator is located, information identifying a particular medical session (e.g., a surgical session) or phase of a particular medical session being performed, information identifying a component of the medical system, information identifying a particular tool or instrument used in the medical session, and information identifying a particular medical system associated with the beacon.

By generating medical facility metrics data that associate the information included in the detected beacon with the tracked events, the beacon-based metrics system enables automatic location-based and/or medical procedure-based tracking of medical personnel, as well as other context-rich tracking of medical facility metrics. For example, the medical facility metrics data generated by the beacon-based metrics system may indicate a particular location where a tracked event occurred, such as a particular operating room, near a particular component of a computer-assisted surgical system, etc. Additionally or alternatively, the medical facility metrics data generated by the beacon-based metrics system may specify a particular medical session during which a tracked event occurred, and/or may specify a particular medical system associated with the tracked events.

Such medical facility metrics data may be used to track and assess user behavior and/or efficiency of medical procedures. For example, the medical facility metrics data may be used to determine time spent by medical personnel performing a certain surgical procedure or various tasks within a surgical procedure, medical personnel efficiency in performing certain tasks, efficiency of specific medical teams, inefficiencies in performing certain tasks during a medical procedure, and the like. The metrics may be used to create/refine best practices, identify areas of expertise and/or improvement for medical facility personnel, and/or otherwise improve operation of a medical facility.

Medical facility metrics data generated by the beacon-based metrics systems described herein may be used to improve the operations of a medical facility. For example, the medical facility metrics data may be used to customize and/or preconfigure features and settings of a mobile application executed by a user device, customize and/or preconfigure features and settings of a medical system (e.g., a computer-assisted surgical system), optimize scheduling of medical personnel, rate an effectiveness and/or efficiency of medical personnel, and any other processes that may identify and correct or otherwise mitigate inefficiencies.

The systems and methods described herein may provide various benefits. For example, the systems and methods described herein may automatically track events associated with a user device and generate medical facility metrics data based on the tracked events. The medical facility metrics data associates the tracked events with information included in a beacon detected by the user device, thus providing context to the tracked events. For example, the medical facility metrics data may indicate the particular locations, medical systems, medical sessions, and medical personnel associated with tracked events. Moreover, the systems and methods described herein may automatically generate the medical facility metrics data without requiring manual tracking and logging of events. Furthermore, the granular level of context in the medical facility metrics data may be used to improve operations of the medical facility. These and other benefits of the systems and methods described herein will be made apparent in the description that follows.

The beacon-based metrics systems and methods described herein may be implemented as part of or in conjunction with a medical system, such as a computer-assisted surgical system. As such, an exemplary computer-assisted surgical system will now be described. The following exemplary computer-assisted surgical system is illustrative and not limiting, as the beacon-based metrics systems and methods described herein may be implemented as part of or in conjunction with other suitable medical systems.

FIG. 1 illustrates an exemplary computer-assisted surgical system 100 ("surgical system 100"). As shown, surgical system 100 may include a manipulating system 102, a user control system 104, and an auxiliary system 106 communicatively coupled one to another. In some examples, surgical system 100 may be implemented by one or more of these components. However, surgical system 100 is not limited to these components, and may include additional components as may suit a particular implementation, such as but not limited to a patient operating table, third-party components (e.g., electrosurgical units) connected to surgical system 100, and the like.

Surgical system 100 may be utilized by a surgical team to perform a computer-assisted surgical procedure on a patient 108. As shown, the surgical team may include a surgeon 110-1, an assistant 110-2, a nurse 110-3, and an anesthesiologist 110-4, all of whom may be collectively referred to as "surgical team members 110." Additional or alternative surgical team members may be present during a surgical session as may serve a particular implementation.

While FIG. 1 illustrates an ongoing minimally invasive surgical procedure, surgical system 100 may similarly be used to perform open surgical procedures or other types of surgical procedures that may similarly benefit from the accuracy and convenience of surgical system 100. Additionally, it will be understood that the surgical session throughout which surgical system 100 may be employed may not only include an operative phase of a surgical procedure, as is illustrated in FIG. 1, but may also include preoperative, postoperative, and/or other suitable phases of the surgical procedure. A surgical procedure may include any procedure in which manual and/or instrumental techniques are used on a patient to investigate, diagnose, or treat a physical condition of the patient. Additionally, a surgical procedure may include any non-clinical procedure, e.g., a procedure that is not performed on a live patient, such as a calibration or testing procedure, a training procedure, and an experimental or research procedure.

As shown in FIG. 1, manipulating system 102 may include a plurality of manipulator arms 112 (e.g., manipulator arm 112-1 through 112-4) to which a plurality of surgical instruments (not shown in FIG. 1) may be coupled. Each surgical instrument may be implemented by any suitable therapeutic instrument (e.g., a tool having tissue-interaction functions), imaging device (e.g., an endoscope), diagnostic instrument, or the like that may be used for a computer-assisted surgical procedure (e.g., by being at least partially inserted into patient 108 and manipulated to perform a computer-assisted surgical procedure on patient 108). In some examples, one or more of the surgical instruments may include force-sensing and/or other sensing capabilities. While manipulating system 102 is depicted and described herein as including four manipulator arms 112, it will be recognized that manipulating system 102 may include only a single manipulator arm 112 or any other number of manipulator arms as may serve a particular implementation.

Manipulator arms 112 and/or surgical instruments attached to manipulator arms 112 may include one or more sensors (e.g., displacement transducers, orientational sensors, positional sensors, etc.) used to generate (i.e., uncorrected) kinematics information (hereinafter "surgical system sensors"). Kinematics information may include information such as pose (e.g., position and/or orientation), movement (e.g., velocity, direction, acceleration, etc.), state (e.g., open, closed, stowed, etc.), and/or other attributes of manipulator arms 112, surgical instruments coupled to manipulator arms 112, and/or any other components of manipulating system 102 (e.g., boom arms). One or more components of surgical system 100 may be configured to use the kinematics information to track (e.g., determine poses, movements, and/or states of) and/or control manipulator arms 112 and/or surgical instruments. Manipulating system 102 may also include other sensors configured to generate other information as may suit a particular implementation. Such sensors may also be referred to as "surgical system sensors" and may include, for example, draping sensors, boom height sensors, and the like.

Surgical instruments attached to manipulator arms 112 may each be positioned at a surgical area associated with a patient. A "surgical area" may, in certain examples, be entirely disposed within a patient and may include an area within the patient at or near where a surgical procedure is planned to be performed, is being performed, or has been performed. For example, for a minimally invasive surgical procedure being performed on tissue internal to a patient, the surgical area may include the tissue, anatomy underlying the tissue, as well as space around the tissue where, for example, surgical instruments being used to perform the surgical procedure are located. In other examples, a surgical area may be at least partially disposed external to the patient at or near where a surgical procedure is planned to be performed, is being performed, or has been performed on the patient. For instance, surgical system 100 may be used to perform an open surgical procedure such that part of the surgical area (e.g., tissue being operated on) is internal to the patient while another part of the surgical area (e.g., a space around the tissue where one or more surgical instruments may be disposed) is external to the patient. A surgical instrument may be referred to as being positioned or located at or within a surgical area when at least a portion of the surgical instrument (e.g., a distal portion of the surgical instrument) is located within the surgical area.

User control system 104 may be configured to facilitate control by surgeon 110-1 of surgical system 100 (e.g., manipulator arms 112 and surgical instruments attached to manipulator arms 112). For example, surgeon 110-1 may interact with user input devices included in user control system 104 to remotely move or manipulate manipulator arms 112 and the surgical instruments coupled to manipulator arms 112. To this end, user control system 104 may provide surgeon 110-1 with imagery (e.g., high-definition stereoscopic imagery) of a surgical area associated with patient 108 as captured by an imaging device (e.g., a stereoscopic endoscope). Surgeon 110-1 may utilize the imagery to perform one or more procedures with one or more surgical instruments coupled to manipulator arms 112.

To facilitate control of surgical instruments, user control system 104 may include a set of master controls (not shown in FIG. 1). These master controls may be manipulated by surgeon 110-1 to control movement of surgical instruments (e.g., by utilizing robotic and/or teleoperation technology). The master controls may be configured to detect a wide variety of hand, wrist, and finger movements by surgeon

110-1. In this manner, surgeon 110-1 may intuitively perform a surgical procedure using one or more surgical instruments.

User control system 104 may further be configured to facilitate control by surgeon 110-1 of other components of surgical system 100. For example, surgeon 110-1 may interact with user control system 104 to change a configuration or operating mode of surgical system 100, to change a display mode of surgical system 100, to generate additional control signals used to control surgical instruments attached to manipulator arms 112, to facilitate switching control from one surgical instrument to another, or to perform any other suitable operation. To this end, user control system 104 may also include one or more additional user input devices (e.g., foot pedals, buttons, switches, touchscreen displays, etc.) configured to receive manual input from surgeon 110-1. In some examples, user control system 104 may also include one or more audio input devices (e.g., microphones) configured to receive audio input (e.g., voice input) from one or more users, and one or more audio output devices (e.g., speakers).

Auxiliary system 106 may include one or more computing devices configured to perform primary processing operations of surgical system 100. The one or more computing devices included in auxiliary system 106 may control and/or coordinate operations performed by various other components (e.g., manipulating system 102 and/or user control system 104) of surgical system 100. For example, a computing device included in user control system 104 may transmit instructions to manipulating system 102 by way of the one or more computing devices included in auxiliary system 106. As another example, auxiliary system 106 may receive, from manipulating system 102 (e.g., from an imaging device), and process image data representative of imagery captured by an endoscope attached to a manipulator arm 112.

In some examples, auxiliary system 106 may be configured to present visual content to surgical team members 110 who may not have access to the imagery provided to surgeon 110-1 at user control system 104. To this end, auxiliary system 106 may include a display monitor 114 configured to display one or more user interfaces, such as images (e.g., 2D images) of the surgical area, information associated with patient 108 and/or the surgical procedure, and/or any other visual content as may serve a particular implementation. For example, display monitor 114 may display images of the surgical area together with additional content (e.g., graphical content, contextual information, etc.) concurrently displayed with the images. In some embodiments, display monitor 114 is implemented by a touchscreen display with which surgical team members 110 may interact (e.g., by way of touch gestures) to provide user input to surgical system 100.

While auxiliary system 106 is shown in FIG. 1 as a separate system from manipulating system 102 and user control system 104, auxiliary system 106 may be included in, or may be distributed across, manipulating system 102 and/or user control system 104. Additionally, while user control system 104 has been described as including one or more user input devices and/or audio input devices, other components of surgical system 100 (e.g., manipulating system 102 and/or auxiliary system 106) may include user input devices, audio input devices, and/or audio output devices as may suit a particular implementation.

Manipulating system 102, user control system 104, and auxiliary system 106 may be communicatively coupled one to another in any suitable manner. For example, as shown in FIG. 1, manipulating system 102, user control system 104, and auxiliary system 106 may be communicatively coupled by way of control lines 116, which may represent any optical, wired, or wireless communication link as may serve a particular implementation. To this end, manipulating system 102, user control system 104, and auxiliary system 106 may each include one or more optical, wired, or wireless communication interfaces, such as one or more local area network interfaces, Wi-Fi network interfaces, cellular interfaces, etc.

Figure 2:
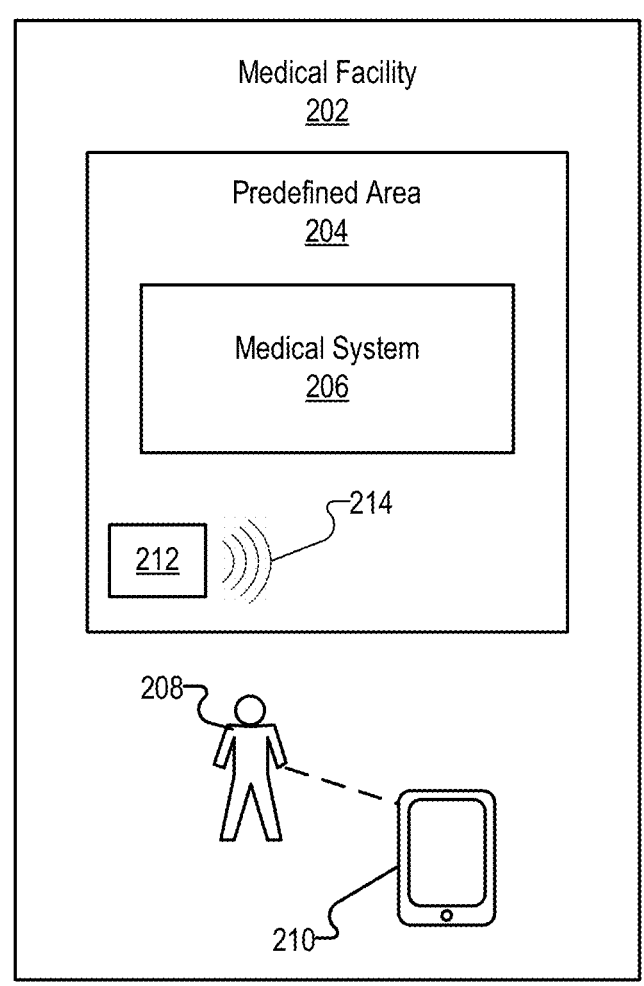
FIGS. 2-6 illustrate exemplary configurations of a medical facility including one or more beacon generators located within a predefined area according to principles described herein.

In some examples a medical system (e.g., surgical system 100) may be located within a medical facility that uses one or more beacons to facilitate pairing of one or more user devices with the medical system and/or provide contextual information about the medical system, about a medical procedure performed with the medical system, and/or about the location of the medical system. FIG. 2 illustrates an exemplary configuration 200 of a medical facility 202. As shown, medical facility 202 includes a predefined area 204 and a medical system 206 located within predefined area 204. Medical facility 202 may be, for example, a hospital, a unit within a hospital (e.g., an emergency room, a trauma center, a maternity unit, an intensive care unit, etc.), a surgical facility, a deployable field hospital, a medical clinic, a doctor's office, a dentist's office, a nursing home, a hospice facility, a rehab facility, an assisted living facility, or any other similar facility. Predefined area 204 is a particular area (e.g., a particular room) within medical facility 202 in which medical system 206 is located and/or used to perform one or more tasks or operations with respect to a patient. For example, predefined area 204 may be an operating room, a recovery room, a consulting room, a patient room, an examination room, an equipment room, and the like. In some examples predefined area 204 is defined by and/or separated from other areas of medical facility 202 (e.g., from an adjoining operating room, from a hallway, from an equipment room, etc.) by one or more physical barriers (e.g., walls, windows, doors, curtains, etc.).

Medical system 206 may be any type of medical system that may be used to monitor, treat, and/or assist a patient located within medical facility 202. For example, medical system 206 may be a surgical system (e.g., a computer-assisted surgical system, such as surgical system 100), an imaging system (e.g., a computed tomography (CT) scanner, a magnetic resonance imaging (MRI) scanner, an X-ray machine, etc.), a dialysis machine, a heart-lung machine, a monitoring device (e.g., a heartrate monitor, a blood pressure monitor, etc.), a ventilator, a patient bed, and the like.

A user 208 (e.g., a surgical team member 110) located within medical facility 202 may gain access, by way of a user device 210, to one or more functional features (e.g., an endoscopic video feed, a settings menu, medical system controls, etc.) associated with medical system 206 when user device 210 is communicatively paired with medical system 206. For example, the user may, by way of an application executed by user device 210, view content associated with medical system 206, interact with medical system 206, and/or communicate with other users via additional user devices that are communicatively paired with medical system 206. Even when user device 210 is not communicatively paired with medical system 206, user 208 may have access to other functional features associated with medical facility 202. For example, the user may, by way of an application executed by user device 210, view and/or edit medical personnel information, update user profile information, view training content, schedule tasks, schedule medical procedures, view patient information, and the like.

User device 210 may be any device capable of presenting information to a user, whether in visual, audio, or haptic format, and/or receiving user input from user 208. For example, user device 210 may be implemented by a mobile device (e.g., a mobile phone, a handheld device, a tablet computing device, a laptop computer, a personal computer, etc.), an audio device (e.g., a speaker, earphones, etc.), a wearable device (e.g., a smartwatch device, an activity tracker, a head-mounted display device, a virtual or augmented reality device, etc.), and/or a display device (e.g., a television, a projector, a monitor, a touch screen display device, etc.).

To convey contextual information to user device 210 and/or to facilitate communicative pairing of user device 210 with medical system 206, a beacon generator 212 is located within predefined area 204 and configured to generate and emit a beacon 214. Beacon 214 may comprise any suitable push signal, or combination of push signals, that may be detected by user device 210. For example, beacon 214 may include ultrasonic signals, electromagnetic signals (e.g., infrared, radio-frequency identification (RFID), etc.), wireless data signals (e.g., Bluetooth, near-field communication, Wi-Fi, etc.), and the like. Additionally, beacon 214 may be emitted at any suitable timing, such as continuous, intermittent, periodic, random, in response to the occurrence of certain events (e.g., manual activation of a button on beacon generator 212), etc.

In examples in which beacon 214 comprises ultrasonic signals, the ultrasonic signals may have any frequency above the human audible hearing range (e.g., above about 18 kHz). In some examples the ultrasonic signals have a frequency greater than about 20 kHz. User device 210 may be configured to detect (e.g., via a microphone) ultrasonic signals in beacon 214 when user device 210 is in proximity to beacon generator 212. For example, ultrasonic beacons may be configured to not transmit through solid barriers (e.g., walls). Accordingly, user device 210 may be configured to detect ultrasonic signals in beacon 214 only when user device 210 is located within the same predefined area (e.g., operating room) as beacon generator 212.

In some examples beacon 214 is configured to include information (e.g., contextual information and/or identification information). For example, beacon generator 212 (e.g., an ultrasonic transducer) may encode the information in an ultrasonic beacon by modulating one or more of the amplitude, frequency, and waveform of ultrasonic signals (e.g., based on binary phase-shift keying (BPSK), quadrature phase-shift keying (QPSK), quadrature amplitude modulation (QAM), and orthogonal frequency division multiplexing modulation (OFDM) methods), by using an audio QR code format, by multi-frequency bit-coding, and the like.

In some examples the information associates, or may be used to associate, beacon 214 with medical system 206. For example, beacon 214 may include a location identifier that identifies the predefined area (i.e., predefined area 204) in which beacon 214 (or beacon generator 212) is located. The location identifier may be, for example, a unique identification ("ID") number (e.g., a room number) assigned to or otherwise representative of predefined area 204. As another example, beacon 214 may include a medical system identifier (e.g., a surgical system identifier) that identifies the medical system (i.e., medical system 206) with which beacon 214 is associated. The medical system identifier may be a unique medical system ID assigned to or otherwise representative of medical system 206. As yet another example, beacon 214 may include a beacon generator identifier that identifies the particular beacon generator (i.e., beacon generator 212) that emits beacon 214. The beacon generator identifier may be a beacon generator ID assigned to or otherwise representative of beacon generator 212. As a further example, beacon 214 may include a medical session identifier that identifies a particular medical session with which beacon 214 is associated. The medical session identifier may be a medical session ID assigned to or otherwise representative of a particular medical session (e.g., a patient ID, medical team personnel IDs, a surgeon ID, a room ID, a surgical session ID, etc.). It will be recognized that the foregoing information that may be included in beacon 214 is merely illustrative and not limiting, as beacon 214 may include any other suitable information (e.g., a network address, GPS coordinates, etc.).

As shown in FIG. 2, beacon generator 212 is a standalone device separate from medical system 206 (e.g., beacon generator 212 is not physically integrated with or controlled by medical system 206). As a standalone device beacon generator 212 may be fixedly positioned at any suitable location within predefined area 204, such as on a wall or ceiling of predefined area 204. Alternatively, beacon generator 212 may be a movable standalone device that may be moved and positioned as desired within predefined area 204 and/or within medical facility 202.

Figure 3:
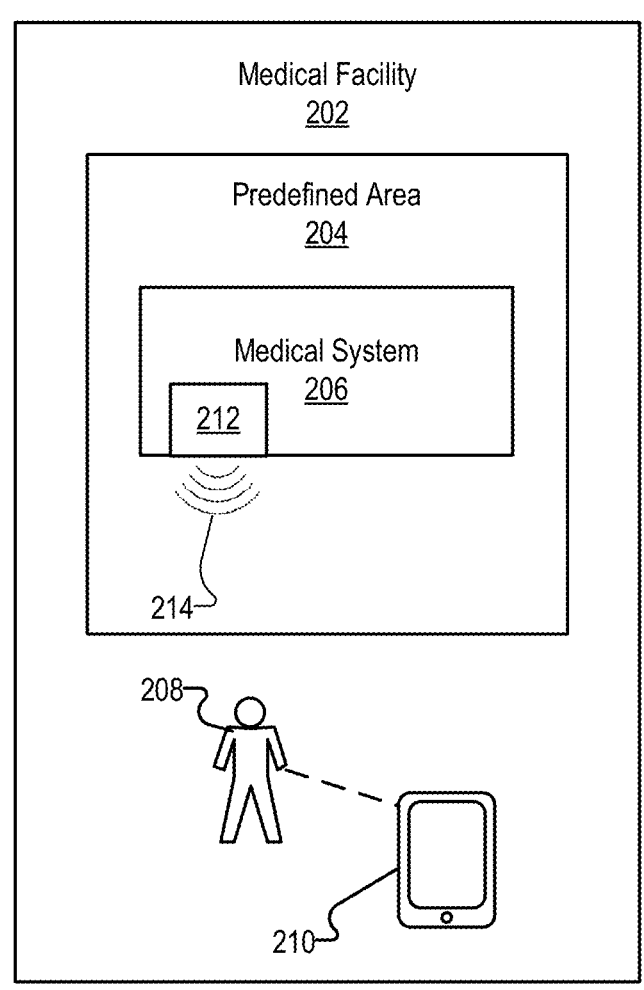

Alternatively to a standalone device separate from medical system 206, beacon generator 212 may be included in medical system 206, as shown in FIG. 3. FIG. 3 illustrates another exemplary configuration 300 of medical facility 202. FIG. 3 is similar to FIG. 2 except that beacon generator 212 is included in medical system 206. Beacon generator 212 may be included in medical system 206 in any suitable way. For example, beacon generator 212 may be physically integrated with medical system 206 (e.g., mounted on a column of manipulating system 102, included in user control system 104, etc.). Thus, if medical system 206 is moved to a different area of medical facility 202, beacon generator 212 also moves to the new area. Additionally or alternatively, beacon generator 212 may be controlled by medical system 206. For example, medical system 206 (e.g., auxiliary system 106 of surgical system 100) may configure beacon 214 to include information and may control the emission of beacon 214 by beacon generator 212.

Figure 4:
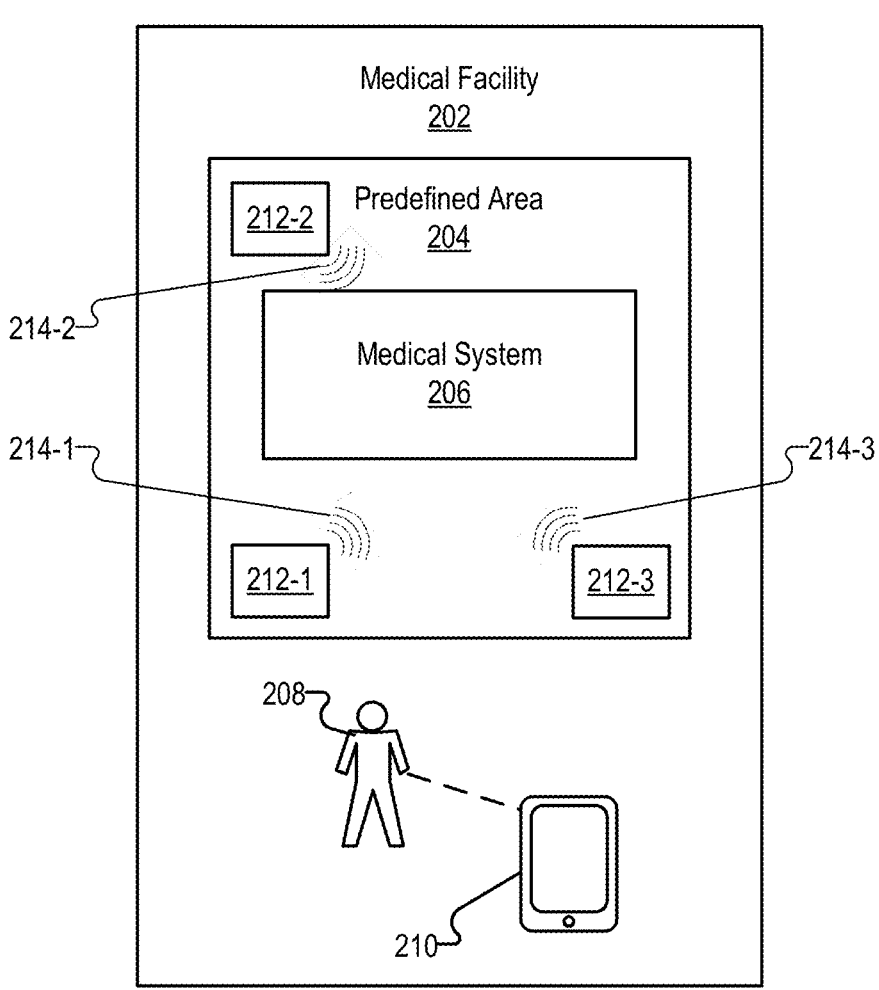

The exemplary configurations 200 and 300 of medical facility 202 described above include a single beacon generator 212 located within predefined area 204. However, multiple beacon generators 212 may be located within predefined area 204, as illustrated in FIG. 4. FIG. 4 illustrates another exemplary configuration 400 of medical facility 202. FIG. 4 is similar to FIG. 2 except that predefined area 204 includes three beacon generators 212 (e.g., beacon generators 212-1 through 212-3) configured to emit beacons 214 (e.g., beacons 214-1 through 214-3). It will be recognized, however, that predefined area 204 may include any other number of beacon generators 212 as may suit a particular implementation.

Beacons 214 may each include information that may be used by a beacon-based metrics system to provide context to tracked events associated with user device 210. In some examples beacons 214 each include the same information (e.g., the same location ID). In additional or alternative examples, each beacon 214 includes unique identification information. For example, beacon 214-1 may include a surgical system identifier, beacon 214-2 may include a location identifier, and beacon 214-3 may include a medical session identifier such as a patient identifier.

Figure 5:
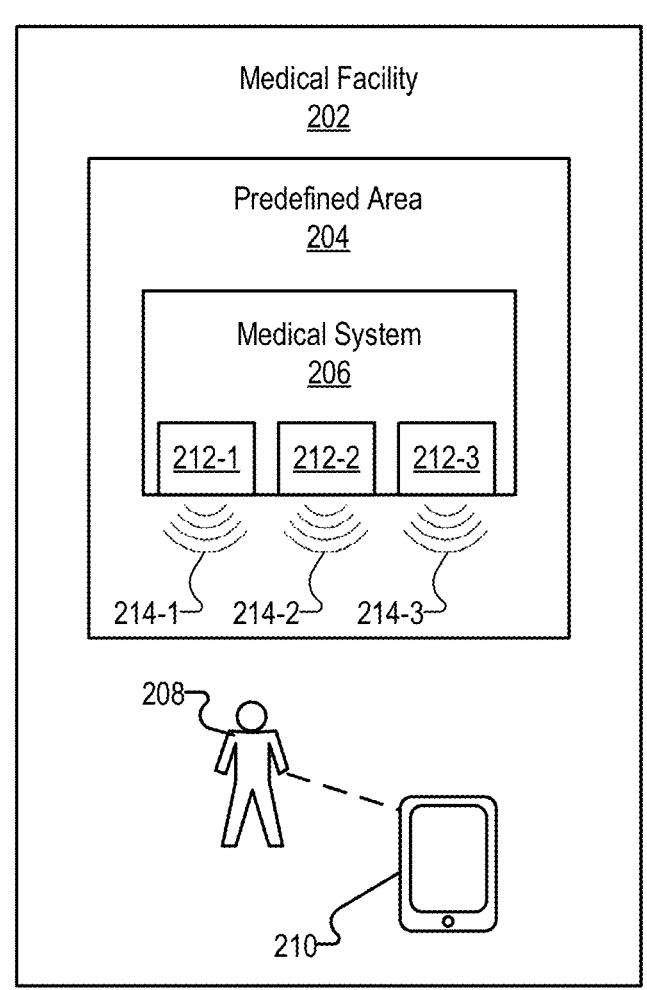

In some examples multiple beacon generators 212 may be included in medical system 206, as shown in FIG. 5. FIG. 5 illustrates another exemplary configuration 500 of medical facility 202. FIG. 5 is similar to FIG. 4 except that beacon generators 212 (e.g., beacon generators 212-1 through 212-3) are included in medical system 206. Beacon generators 212 may be included in medical system 206 in any suitable way. For example, beacon generators 212 may be physically integrated with and/or controlled by medical system 206, as explained above. In some examples each beacon generator 212 is included in a different component of medical system 206. For instance, if medical system 206 is implemented by surgical system 100, beacon generator 212-1 may be included in manipulating system 102, beacon generator 212-2 may be included in user control system 104, and beacon generator 212-3 may be included in auxiliary system 106.

In some examples beacons 214 include the same information (e.g., the same medical system ID). In additional or alternative examples, each beacon 214 includes unique information. For example, when medical system 206 includes multiple components, various components may each include a beacon generator 212 and each beacon 214 may include a unique component identifier (e.g., a component ID) assigned to or otherwise representative of the particular component in which the beacon generator 212 is included. For instance, referring again to the example in which medical system 206 is implemented by surgical system 100, beacon 214-1 may include a unique component ID for manipulating system 102, beacon 214-2 may include a unique component ID for user control system 104, and beacon 214-3 may include a unique component ID for auxiliary system 106.

Figure 6:
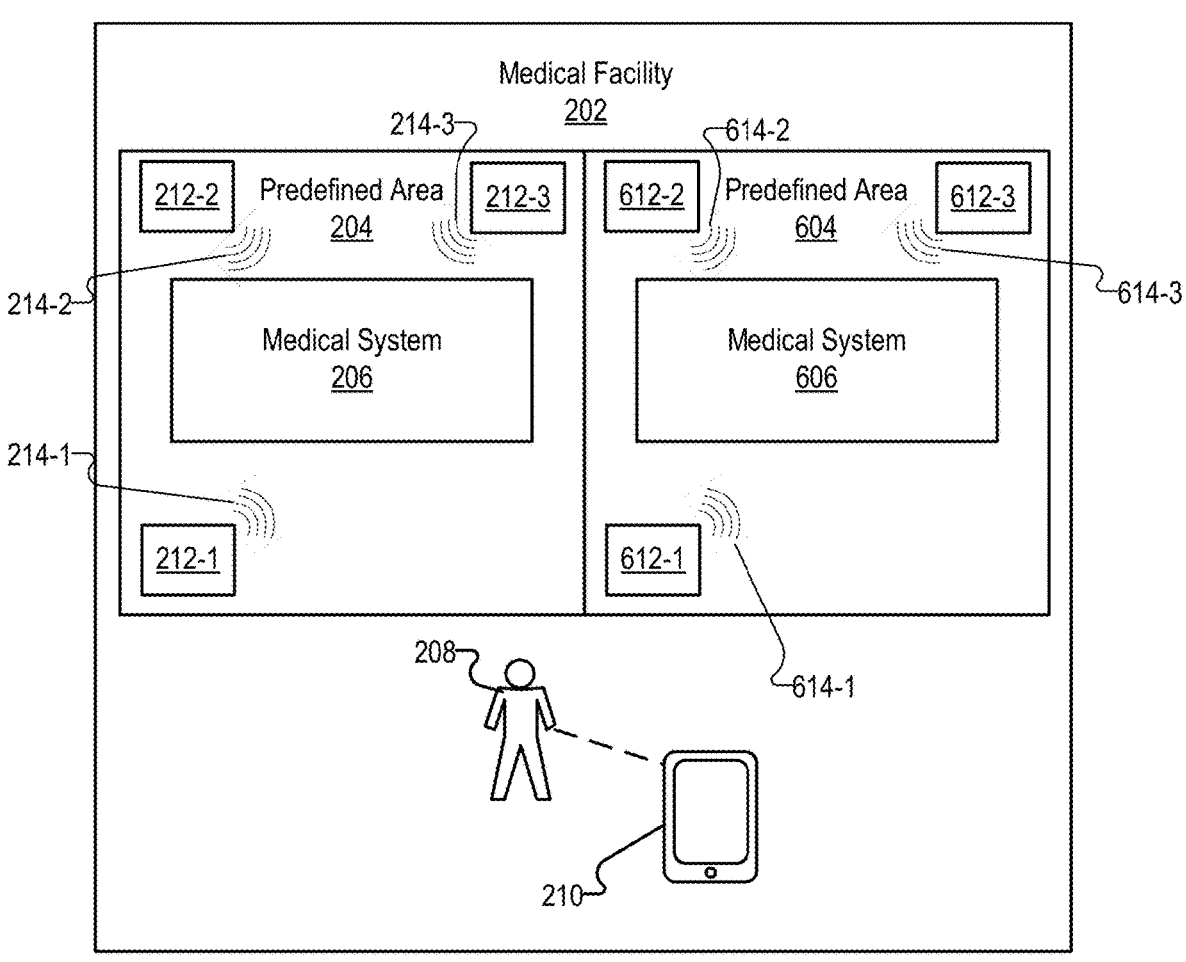

In additional configurations medical facility 202 may also include additional beacon generators (not shown in FIGS. 4 and 5) in areas outside of predefined area 204, as illustrated in FIG. 6. FIG. 6 illustrates another exemplary configuration 600 of medical facility 202. FIG. 6 is similar to FIG. 4 except that medical facility 202 includes an additional predefined area 604 adjoining predefined area 204, additional beacon generators 612 (e.g., beacon generators 612-1 through 612-3) located within predefined area 604 and that emit beacons 614 (e.g., beacons 614-1 through 614-3), and an additional medical system 606 located within predefined area 604. It will be recognized that any of beacon generators 212-1 through 212-3 may alternatively be included in medical system 206, and any of beacon generators 612-1 through 612-3 may alternatively be included in medical system 612, in the manner described above with reference to FIG. 5. Additionally, predefined areas 204 and 604 may each include any other number of beacon generators 212 and 612, respectively, as may suit a particular implementation.

Figure 7:
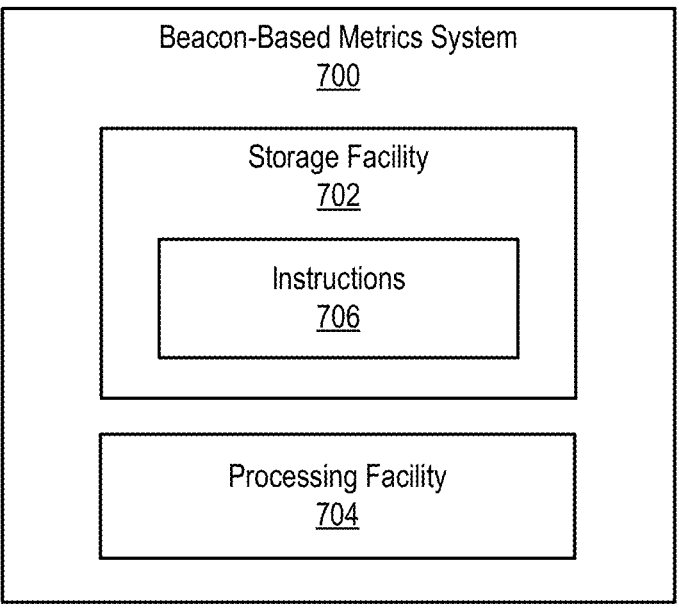
FIG. 7 illustrates an exemplary beacon-based metrics system according to principles described herein.

As mentioned, beacons may include information that may be used by a beacon-based metrics system to provide context to tracked events associated with a user device. FIG. 7 illustrates an exemplary beacon-based metrics system 700 ("metrics system 700") that may be configured to generate medical facility metrics data based on tracked events and information included in one or more detected beacons. Metrics system 700 may be included in, implemented by, or connected to any medical systems or other computing systems described herein. For example, metrics system 700 may be implemented by a computer-assisted surgical system (e.g., surgical system 100). As another example, metrics system 700 may be implemented by a stand-alone computing system communicatively coupled to a medical system. In some examples metrics system 700 may be implemented, in whole or in part, by a user device (e.g., user device 210).

As shown in FIG. 7, metrics system 700 includes, without limitation, a storage facility 702 and a processing facility 704 selectively and communicatively coupled to one another. Facilities 702 and 704 may each include or be implemented by hardware and/or software components (e.g., processors, memories, communication interfaces, instructions stored in memory for execution by the processors, etc.). For example, facilities 702 and 704 may be implemented by any component in a medical system. In some examples, facilities 702 and 704 may be distributed between multiple devices and/or multiple locations as may serve a particular implementation.

Storage facility 702 may maintain (e.g., store) executable data used by processing facility 704 to perform any of the operations described herein. For example, storage facility 702 may store instructions 706 that may be executed by processing facility 704 to perform any of the operations described herein. Instructions 706 may be implemented by any suitable application, software, code, and/or other executable data instance. Storage facility 702 may also maintain any data received, generated, managed, used, and/or transmitted by processing facility 704.

Processing facility 704 may be configured to perform (e.g., execute instructions 706 stored in storage facility 702 to perform) various operations associated with pairing a user device with a medical system. For example, processing facility 704 may be configured to track events associated with a user device located within a medical facility. Processing facility 704 may also determine that the user device detects a beacon emitted by a beacon generator located within the medical facility and identify information included in the beacon. Processing facility 704 may generate medical facility metrics data representative of the tracked events by associating the information included in the beacon with a set of tracked events that occur during a time period in which the user device detects the beacon. These and other operations that may be performed by processing facility 704 are described herein. In the description that follows, any references to operations performed by metrics system 700 may be understood to be performed by processing facility 704 of metrics system 700.

In some exemplary implementations, metrics system 700 is implemented entirely by the medical system itself. For example, metrics system 700 may be implemented by one or more computing devices included in medical system 206 (e.g., in one or more computing devices included within manipulating system 102, user control system 104, and/or auxiliary system 106 of surgical system 100).

Figure 8:
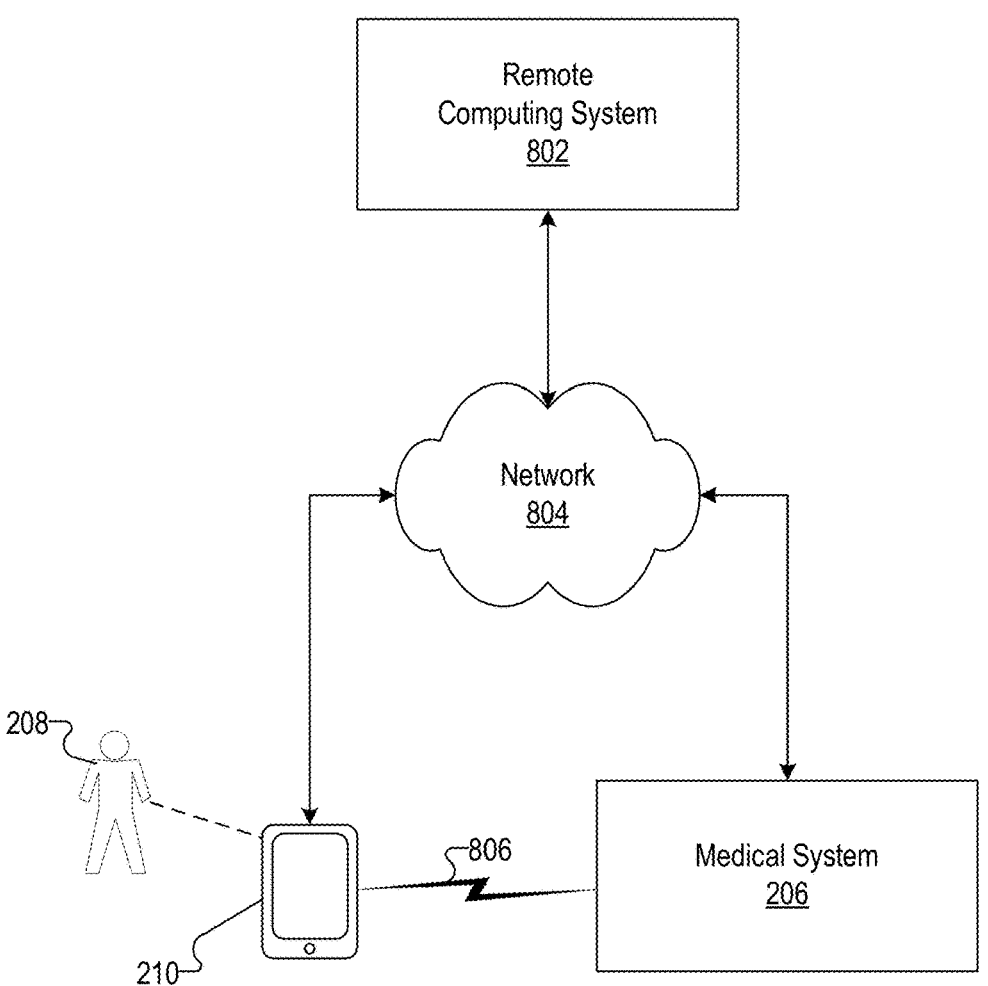
FIG. 8 illustrates an exemplary implementation of the beacon-based metrics system of FIG. 7 according to principles described herein.

FIG. 8 illustrates another exemplary implementation 800 of metrics system 700. In implementation 800, a remote computing system 802 may be communicatively coupled to medical system 206 by way of a network 804. Remote computing system 802 may include one or more computing devices (e.g., servers) configured to perform any of the operations described herein.

Network 804 may be a local area network, a wireless network (e.g., Wi-Fi), a wide area network, the Internet, a cellular data network, and/or any other suitable network. Data may flow between components connected to network 804 using any communication technologies, devices, media, and protocols as may serve a particular implementation.

As shown, user device 210 may be connected to network 804 and thereby communicate with remote computing system 802. In some examples, user device 210 may also be communicatively paired with medical system 206. When user device 210 is communicatively paired with medical system 206, user device 210 may be configured to exchange data with medical system 206, thereby enabling user 208 to access, by way of user device 210, one or more functional features associated with medical system 206.

User device 210 may be communicatively paired with medical system 206 in any suitable way. For example, user device 210 may be communicatively paired with medical system 206 by way of an indirect communication link (e.g., by way of remote computing system 802 and/or network 804). Alternatively, user device 210 may be communicatively paired with medical system 206 by way of a direct (e.g., peer-to-peer, single hop, or ad hoc) communication link 806. The direct communication link may include, for example, a direct wireless connection, such as a Bluetooth connection, a near field communication connection, a Wi-Fi connection, a Wi-Fi Direct connection, a smartphone ad hoc network (SPAN) connection, a mobile device ad hoc network (MANET) connection, etc. In some examples user device 210 may be communicatively paired with medical system 206 only when user device 210 is physically proximate to medical system 206, such as when user device 210 detects an ultrasonic beacon associated with medical system 206 (e.g., beacon 214). It will be recognized, however, that in some examples user device 210 is not communicatively paired with medical system 206.

In some examples remote computing system 802 and/or network 804 are located partly or entirely within a medical facility (e.g., medical facility 202) as part of a medical facility management system (not shown). A medical facility management system may include one or more computing systems configured to generate and/or maintain medical facility data associated with the medical facility and its operations, such as data representative of medical systems included in the medical facility and locations of the medical systems, patient information, beacon generator information and locations of the beacon generators, medical session information, medical personnel information, schedule information, and the like.

In some examples, metrics system 700 is entirely implemented by remote computing system 802 or user device 210. In alternative examples metrics system 700 is distributed across any two or more of remote computing system 802, medical system 206, and user device 210.

Various operations that may be performed by metrics system 700 (e.g., by processing facility 704 of metrics system 700), and examples of these operations, will now be described. It will be recognized that the operations and examples described herein are merely illustrative of the many different types of operations that may be performed by metrics system 700.

Metrics system 700 may track events associated with a user device (e.g., user device 210) located within a medical facility (e.g., medical facility 202). In certain examples, events associated with a user device may include beacon detection events ("detection events"), user interaction events ("interaction events"), and/or medical system response events ("response events"), as will now be described in detail.

Detection events include detection (or non-detection), by the user device (e.g., user device 210), of a beacon (e.g., beacon 214) emitted by a beacon generator (e.g., beacon generator 212) located within a medical facility (e.g., medical facility 202). The user device may detect a beacon in any suitable way. For example, the user device may include a microphone configured to detect ambient sound waves, including ultrasonic beacons, and process the detected ambient sound waves to generate audio signals representative of the detected ambient sound waves. Additionally or alternatively, the user device may be equipped with an ultrasonic sensor configured to detect the range of ultrasonic beacons emitted in the medical facility. In some examples an application executed by the user device may process the audio signals to filter out audio signals that do not meet a predefined set of criteria (e.g., audio signals that are not in the ultrasonic range, do not fall within a predefined amplitude range, etc.). The microphone (or ultrasonic sensor) may also be set, either automatically by the application or manually by a user, to an "always-on" state. In this way the user device may continually scan for ultrasonic beacons while the user device is moving throughout a medical facility. While in the "always-on" state the user device may sample for ultrasonic beacons at any suitable sampling rate (e.g., 30 Hz). Alternatively to the "always-on" state, the user device may sample for ultrasonic beacons only in response to a user push input (e.g., user input directing the user device to scan for ultrasonic beacons).

In some examples the user device (e.g., an application executed by the user device) analyzes the audio signals to determine whether the audio signals include an ultrasonic beacon. The user device may use any suitable sound processing algorithm to determine whether the audio signals include an ultrasonic beacon. In alternative examples, metrics system 700 may access the audio signals from the user device and analyze the accessed audio signals to determine whether the audio signals include an ultrasonic beacon. Metrics system 700 may use any suitable sound processing algorithm to determine whether the audio signals include an ultrasonic beacon. In some examples the user device may be configured to periodically (e.g., every 5 seconds) transmit the audio signals to metrics system 700.

Exemplary detection events will now be illustrated with reference to FIGS. 2 and 9. FIG. 9 shows another exemplary configuration 900 of medical facility 202. FIG. 9 is similar to FIG. 2 except that user 208 and user device 210 have moved into predefined area 204, such as to perform a medical procedure (e.g., a minimally invasive surgical procedure) with medical system 206 (e.g., surgical system 100). While user 208 and user device 210 are located outside of predefined area 204 (see FIG. 2), user device 210 is out of the detection range of beacon 214 (e.g., an ultrasonic beacon) and thus does not detect beacon 214. After user 208 moves into predefined area 204 with user device 210, user device 210 is within the detection range of beacon 214 and thus detects beacon 214. Each time that user device 210 detects beacon 214 may be logged by user device 210 as a detection event. For example, if user 208 and user device 210 are located within predefined area 204 for five minutes and user device 210 samples at a rate of 10 Hz, user device 210 and/or metrics system 700 may log 3,000 detection events.

User interaction events include distinct interactions, by a user, with the user device. In some examples user interaction events include user interactions with an application executed by the user device, such as user selection of menu options, user selection of hyperlinks and other selectable options, user control of video or audio playback features, user input of information, and the like.

The application executed by the user device may include any type of application, such as a messaging application, a phone application, a media application, a browser application, a social media application, etc. Accordingly, user interaction events may include, for example, each instance of a user interacting with the user device by way of the application to view or send a text message, play media content (e.g., via YouTube, Spotify, etc.), access a social media application (e.g., Instagram, Facebook, Twitter, etc.), post to a social media account, browse the Internet, etc.

In some examples the application executed by the user device is associated with a medical facility and/or a medical system. For example, the application may be communicatively connected with a medical facility management system to provide the user access to view information generated and/or maintained by the medical facility. Such information may include, for example, information about the medical facility (e.g., a map of the medical facility, operating hours of the medical facility, a listing of services provided at the medical facility, etc.), patient information (e.g., patient charts, patient medication information, patient contact information, insurance information, etc.), medical personnel information (e.g., a list of service providers, a list of currently assigned surgical teams, etc.), medical session information (e.g., a list of surgical team members assigned to a particular surgical session, a location of a particular medical session, a type of medical procedure being performed on a particular patient, etc.), medical system information (e.g., a list of available medical systems and equipment, availability of particular medical systems, etc.), and the like. Accordingly, user interaction events may include, for example, each instance of a user interacting with the user device by way of the application to access a patient chart, input information into a patient chart (e.g., dosage information), schedule use of a particular medical system, schedule a particular surgical team to perform a particular surgical session, view a tutorial video for use of a particular medical system, logging completion of a particular task, etc.

In some examples in which the user device is communicatively paired with a medical system, the application executed by the user device may be configured to provide the user with access to functional features associated with the medical system. For example, the application may provide the user with access to media content (e.g., visual content and/or audio content) generated by the medical system, such as an endoscopic video feed generated by surgical system 100, an ultrasound image, an MRI image, a CT scan, an X-ray image, etc. Additionally or alternatively, the application may enable the user to interact with the medical system (e.g., control one or more functional features or settings of the medical system), view and/or update information associated with a particular medical session performed with the medical system, and/or communicate with other users by way of additional user devices that are communicatively paired with the medical system. Accordingly, user interaction events may include, for example, each instance of a user interacting with the user device by way of the application to adjust a medical system setting, view media content generated by the medical system, and control operation of the medical system.

In some examples in which the user device is communicatively paired with the medical system, interaction events may also include distinct interactions, by one or more users, with the medical system. Interaction events may include direct user interactions and/or indirect user interactions with the medical system. A direct user interaction may include any physical interaction, by a user, with a user input device included in the medical system. Examples of direct user interactions with a user input device may include, without limitation, manipulation of master controls, actuation of a medical system button, actuation of a medical system foot pedal, user touch input on a touchscreen display (e.g., display monitor 114, etc.), and the like. Additionally or alternatively, a direct user interaction may include any physical interaction, by a user, with a component of the medical system. For example, direct user interactions with a component of surgical system 100 may include, without limitation, positioning or targeting manipulating system 102 at a patient operating table, manually moving a manipulator arm 112, docking a cannula to a manipulator arm 112, coupling and/or removing a surgical instrument from a manipulator arm 112, inserting a surgical instrument within a patient and/or removing a surgical instrument from the patient, manually re-positioning master controls, and the like.

An indirect user interaction with the medical system may include any non-physical interaction, by a user, with the medical system. Examples of indirect interactions may include, for example, user interactions based on audio (e.g., voice inputs and/or commands provided to the medical system), non-physical interactions with medical system sensors (e.g., moving the user's eyes into a detectable range of an eye sensor included in an image display system), and the like. In some examples, an indirect interaction event may also include the absence of interaction, by a user, with the medical system for a period of time (e.g., for at least three minutes).

As used herein, response events associated with a user device include distinct operations performed by the medical system in response to interaction events. Response events may include any mechanical, electrical, optical, hardware, and/or software-based operations as may serve a particular implementation. For example, response events may include adjustment of a pose of a component of surgical system 100 (e.g., moving a surgical instrument in response to a corresponding operation of a master control, adjusting an ergonomic position of master controls, etc.), operation of a functional feature of the medical system (e.g., energizing a cautery instrument, opening and closing forceps or scissors, firing a stapling instrument, etc.), adjustment of a medical system setting (e.g., adjusting an exposure level or a zoom level of an imaging system, etc.), detection of a system fault or error (e.g., detection of a collision of manipulator arms 112, a collision of surgical instruments, etc.), generation of a fault code, and the like.

As mentioned above, metrics system 700 may track events associated with the user device. The tracking may include collecting and storing (e.g., in a tracked event table maintained in storage facility 702) event data representative of tracked events associated with the user device. Event data may be based on user device event data and/or medical session data. User device event data may include any data representative of events tracked or logged by the user device and/or by the application executed by the user device (e.g., data representative of user interaction events). Metrics system 700 may access user device event data from a data log maintained by the user device and/or an application executed by the user device.

Medical session data may include any data tracked or logged by a medical system or other system communicatively coupled with a medical system (e.g., a medical facility management system). Accordingly, medical session data may be representative of user interaction events (e.g., user interactions with the medical system) and/or response events. Metrics system 700 may access medical session data from a data log maintained by the medical system or another system communicatively connected with the medical system.

The medical session data may be generated by the medical system (e.g., by manipulating system 102, user control system 104, and/or auxiliary system 106 of surgical system 100), by one or more components coupled to the medical system during the medical session, and/or by any other device associated with the medical system as may serve a particular implementation. In scenarios in which metrics system 700 is implemented entirely by remote computing system 802, medical session data may be generated by medical system 206 and transmitted to remote computing system 802 via network 804. Thus, remote computing system 802 may track operations of medical system 206.

Medical session data (e.g., interaction event data and response event data) generated during a medical session may include various types of data associated with interaction events and response events. For example, surgical session data generated during a surgical session performed with a computer-assisted surgical system (e.g., surgical system 100) may include kinematic data, image data, sensor data, surgical instrument data, and/or any other type of data as may serve a particular implementation.

Kinematic data may be representative of a pose of a component within the computer-assisted surgical system and/or a component coupled to the computer-assisted surgical system. For example, kinematic data may be representative of a pose of a manipulator arm 112, a surgical instrument coupled to a manipulator arm 112, master controls, and/or any other component of the computer-assisted surgical system as may suit a particular implementation.

Image data may be representative of one or more images captured by an imaging device coupled to the computer-assisted surgical system. For example, image data may be representative of one or more images captured by an imaging device (e.g., a stereoscopic endoscope) coupled to a manipulator arm 112. The one or more images may constitute one or more still images and/or video captured by the imaging device. In some examples, metrics system 700 may access image data by receiving (e.g., by way of a network) images output by the imaging device. In additional or alternative examples, image data may include image data generated by an imaging device that is external to a patient.

Sensor data may include any data generated by surgical system sensors included in or associated with a computer-assisted surgical system. Sensor data may be representative of any sensed parameter as may serve a particular implementation. In some examples, certain kinematic data and image data may be generated by and/or based on parameters sensed by surgical system sensors. Accordingly, sensor data may include such kinematic data and image data.

Surgical instrument data may include any data generated by a surgical instrument, and may be representative of an identification ("ID") of the surgical instrument, an operational state of the surgical instrument (e.g., open, closed, electrically charged, idle, etc.), a fault code of the surgical instrument, etc.

In some examples, medical session data may also include data representative of information associated with a particular medical session. For example, the medical session data may include data indicating a target anatomy for a particular surgical procedure (e.g., liver, colon, lungs, etc.), a type of medical procedure (e.g., hernia repair, hysterectomy, biopsy, etc.), a time and date of a particular medical procedure, medical personnel information for a particular medical procedure (e.g., user authentication information, a user profile, surgical team member changes, etc.), patient information, and the like.

Metrics system 700 may track the medical session data in any suitable way. For example, in implementation 800, medical system 206 and/or user device 210 may be configured to provide, over time, medical session data to remote computing system 802.

To enhance the tracked events, metrics system 700 may also track other information associated with the user device or the tracked events, such as an identification of the user device (e.g., a device ID), an identification of a user of the user device (e.g., a user ID of a user assigned to the user device, a user logged in to an application executed by the user device, etc.), a role (e.g., surgeon, nurse, assistant, etc.) of the user of the user device, event timing information (e.g., timestamps for particular events, time spent performing various tasks, etc.), user device motion information (e.g., inertial measurement unit (IMU) data), and any other suitable information. As will be explained below, such information may add layers of context to tracked events.

As mentioned above, metrics system 700 may be configured to determine that a user device detects a beacon emitted by a beacon generator located within the medical facility. Metrics system 700 may determine that the user device detects the beacon in any suitable way. As explained above, in some examples the user device may determine whether detected audio signals include an ultrasonic beacon. In these examples the user device may also transmit a notification and the audio signals (e.g., data representative of the ultrasonic beacon) to metrics system 700. In response to receipt of the notification and/or the data representative of the ultrasonic beacon, metrics system 700 may determine that the user device detects an ultrasonic beacon.

As also explained above, in alternative examples metrics system 700 (rather than the user device) may determine whether the detected audio signals include an ultrasonic beacon. In these examples, if metrics system 700 determines that the audio signals include an ultrasonic beacon, metrics system 700 determines that the user device detects an ultrasonic beacon.

Metrics system 700 may also be configured to identify information included in the detected beacon. Metrics system 700 may identify information included in the detected beacon in any suitable way. For example, metrics system 700 may process and analyze audio signals representative of the detected beacon to identify information included in the detected beacon. For instance, metrics system 700 may identify the information included in an ultrasonic beacon by comparing the detected audio signals representative of the ultrasonic beacon with ultrasonic beacon data included in a table of ultrasonic beacon data. The table of ultrasonic beacon data may associate a particular ultrasonic beacon configuration (e.g., a unique combination of amplitude, frequency, waveform, etc.) with a particular instance of information (e.g., a location ID, a medical system ID, a medical session ID, etc.). Metrics system 700 may identify the information included in the detected ultrasonic beacon by identifying, in the table of ultrasonic beacon data, a particular instance of information that is associated with an ultrasonic beacon configuration that matches the detected ultrasonic beacon.

In alternative examples the user device (e.g., an application executed by the user device) may identify the information included in the beacon (e.g., in any of the ways described herein) and transmit data representative of the information to metrics system 700. Metrics system 700 may identify the information included in the beacon based on the data representative of the information transmitted by the user device to metrics system 700.

Metrics system 700 may also be configured to generate medical facility metrics data ("metrics data") based on the tracked events and the information included in the detected beacon. Metrics system 700 may generate the metrics data in any suitable way. In some examples metrics system 700 may generate the metrics data by associating tracked events that occur while the user device detects the beacon with the information included in the detected beacon. To this end metrics system 700 may identify a set of tracked events that occur during a time period in which the user device detects the beacon. This may be done in any suitable way.

In some examples, metrics system 700 may identify the set of tracked events based on timestamps of the tracked events. For instance, metrics system 700 may compare a timestamp of each tracked event with timestamps of detection events and identify tracked events that have a timestamp that occurs near (e.g., within 2 seconds) or between detection event timestamps.

In other examples, metrics system 700 may identify the set of tracked events other than in real-time, such as during a time period in which the user device does not detect the beacon. For example, metrics system 700 may identify a first detection event timestamp and the last detection event timestamp of the period during which the user device detects the beacon. Metrics system 700 may identify the set of tracked events as all tracked events that have a timestamp that occurs between the first detection event timestamp and the last detection event timestamp associated with detection of the beacon.

In further examples, metrics system 700 may identify the set of tracked events in real-time by tracking, in response to a first detection event based on detection of a particular beacon, all events associated with the user device until metrics system 700 determines that the user device no longer detects the beacon. When metrics system 700 determines that the user device no longer detects the beacon, metrics system 700 may cease tracking events associated with the user device.

Metrics system 700 may associate the information included in the beacon with the set of tracked events that occur during the time period in which the user device detects the beacon. For example, metrics system 700 may add, to a table of tracked events, the information included in the detected beacon for each tracked event.

In some examples the generating of the metrics data may further include collecting information from the user device and associating the information from the user device with the set of tracked events. The information collected from the user device may include any suitable information stored and/or maintained by the user device (or by an application executed by the user device). For example, the information may include user device information (e.g., a user device ID), user information (e.g., a user name, user profile information, a user role (e.g., surgeon, nurse, technician, assistant, patient, administrator, etc.)). In this way metrics system 700 may provide additional context to the tracked event data by including information about the user device and/or the user of the user device.

Figure 10:
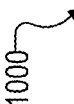
FIG. 10 illustrates an exemplary medical facility metrics data table according to principles described herein.

FIG. 10 illustrates an exemplary table of medical facility metrics data ("metrics table 1000") that may be generated by metrics system 700. Metrics table 1000 may be configured to associate information included in a beacon detected by a user device with tracked events associated with the user device and that occur while the user device detects the beacon.

Metrics table 1000 may be configured to specify one or more tracked events associated with a user device. For example, as shown in column 1002, metrics table 1000 may specify a plurality of distinct tracked events associated with a user device. The tracked events may be tracked, for example, by populating metrics table 1000 with event data collected from the user device and/or a medical system associated with the user device.

Metrics table 1000 may also be configured to specify a timestamp indicating a time when each tracked event occurred. For example, as shown in column 1004, metrics table 1000 may specify a plurality of timestamps associated with distinct tracked events. The timestamps may be included in the event data, or the timestamps may be tracked, for example, by accessing timestamp data from the user device and/or the medical system in real-time when metrics system 700 tracks the events.

Metrics table 1000 may also be configured to specify one or more user device IDs identifying one or more particular user devices associated with the tracked events. For example, as shown in column 1006, metrics table 1000 may specify a plurality of user device IDs associated with distinct tracked events. The user device IDs may be tracked, for example, by accessing user device data from the user device while the user device detects the beacon.

Metrics table 1000 may also be configured to specify a particular user ID of a user of the user device. For example, as shown in column 1008, metrics table 1000 may specify a plurality of user IDs each identifying a particular user of the user device associated with each tracked event.

As shown in FIG. 10, the tracked events includes a first set of tracked events (e.g., "Beacon01_Detected," "User_Login," "Open_Patient_Chart," and "Input_Status") that occur while a first user device (e.g., the user device having a User Device ID of "1234") detects a beacon. The first set of tracked events are associated with a user (e.g., a nurse) having a User ID of "Nurse001." Additionally, the tracked events includes a second set of tracked events (e.g., "Beacon02_Detected," "Targeting_Complete," "Adjust_Arm," and "Arm_Collision") that occur while a second user device (e.g., the user device having a User Device ID of "5678") detects another beacon. The second set of tracked events are associated with a user (e.g., a surgeon) having a User ID of "Surg023." As explained above, metrics system 700 collects data representative of the tracked events and the other tracked information (e.g., timestamps, user device IDs, and user IDs) from the user devices and/or from a medical system associated with one or more user devices.

Metrics table 1000 may also be configured to specify one or more instances of additional information associated with the tracked events. Metrics system 700 may collect data representative of the additional information from the beacon detected by each user device.

For example, as shown in column 1010, metrics table 1000 may specify a plurality of location IDs each identifying a predefined area located within the medical facility. As shown in column 1012, metrics table 1000 may specify a particular medical system associated with one or more tracked events. As shown in column 1014, metrics table 1000 may specify a particular medical session being performed within each predefined area and/or with each medical system.

In metrics table 1000, the first set of tracked events are associated with information (e.g., the location ID) included in the beacon detected by the first user device (e.g., user device "1234"). The second set of tracked events are associated with information (e.g., the location ID, the medical system ID, and the surgical session ID) included in the beacon detected by the second user device (e.g., user device "5678").

It will be recognized that metrics table 1000 is not limited to the examples of data shown in FIG. 10, but may include any additional or alternative data as may suit a particular implementation. For example, metrics table 1000 may associate a medical system component ID representative of a particular medical system component (e.g., manipulating system 102, user control system 104, auxiliary system 106, etc.) with a particular tracked event. Additionally, metrics table 1000 may be dynamically updated as beacon generators or medical systems change locations within the medical facility and as medical sessions change (e.g., start or end).

In the embodiments described above the metrics data specifies, as a location ID, a particular predefined area (e.g., predefined area 204) located within the medical facility (e.g., medical facility 202). In some examples the location tracking of the user device may be enhanced to provide a more localized determination of the user device location. In these examples metrics data may indicate a position of a user device with respect to various medical system components.

For example, a position of a user device with respect to various different components located within a predefined area may be determined based on the detected signal strength of various beacons emitted by multiple beacon generators. This data may be used to track metrics associated with user positioning during a medical session. To illustrate, as shown in FIG. 5 each component of medical system 206 may include a beacon generator 212 (e.g., beacon generators 212-1 through 212-3) that emits an ultrasonic beacon 214 (e.g., ultrasonic beacons 214-1 through 214-3). User device 210 may detect each ultrasonic beacon 214. Based on a relative signal strength and/or other properties of the ultrasonic beacons as detected by the user device 210, metrics system 700 may determine that user device 210 (and hence user 208) is closer to one component than another (e.g., closer to user control system 104). Accordingly, metrics system 700 may associate a component identifier (e.g., a component ID) of the nearest component with tracked events. In metrics table 1000 the component identifier may be indicated in column 1010 in place of the location ID, or it may be included in a new column added to metrics table 1000.

In some examples beamforming may additionally or alternatively be used to further enhance localization of the user device. For example, beacon generators (e.g., beacon generators 212) located within a predefined area (e.g., predefined area 204) or within a medical system (e.g., medical system 206) may be configured to beamform the ultrasonic beacons (e.g., ultrasonic beacons 214). For example, beacon generators 212 may comprise a beamforming speaker array.

In some examples metrics system 700 may enhance the localization of the user device by tracking motion information of the user device. The motion information may include, for example, IMU information that indicates an orientation of the user device. Such information may be used by metrics system 700 to determine that the user device is oriented toward a particular component (e.g., manipulating system 102).

The metrics data generated by metrics system 700 is rich with contextual information that may be used to improve operations of a medical facility. For example, the metrics data may automatically track the location of a user device (e.g., user device 210) and/or medical personnel (e.g., a particular user, a particular type of user (e.g., a surgeon, a nurse, an assistant, etc.), a surgical team, etc.) within medical facility 202, and may automatically track events that occur at particular locations. Additionally or alternatively, the metrics data may automatically track events that occur during one or more medical sessions in which the medical personnel participate. Thus, the metrics data may be used to determine the amount of time that medical personnel were located within a particular area (e.g., an operating room, a break room, etc.), the amount of time that medical personnel participated in a particular medical session or performed specific tasks, the effectiveness of particular medical personnel, etc.

For instance, with reference to FIG. 10, metric table 1000 may indicate that a particular nurse ("NURSE001") was located in room "RM202" (e.g., a nurse's station) for approximately 6.5 minutes (e.g., from time 08:00:53 to time 08:07:22), during which time the nurse accessed a patient chart and updated the patient's status. Metric table 1000 may also indicate that a particular surgeon ("SURG023") entered operating room ("OR003") at 8:23:12 and performed a surgical procedure on a patient ("PATIENT_A") and left the operating room at 9:22:07. Thus, metric table 1000 indicates that the surgeon performed the surgical procedure on the patient in approximately one hour. Metric table 1000 also indicates that, during the surgical procedure, the surgeon adjusted manipulator arms in a manner that caused a collision between manipulator arms.

The metrics data may be used (e.g., by a medical facility management system) in many different ways to improve operations of the medical facility. For example, the metrics data may indicate that a particular user spends an excessive amount of time in a breakroom and interacting with social media applications on the user device. Accordingly, the medical facility management system may flag the particular user's profile for review, automatically schedule the particular user for additional medical sessions, disable certain applications on the user device, and/or direct the user device to notify the user that an allotted break time has expired.

As another example, the metrics data may indicate that a particular surgical team regularly performs a particular type of surgical procedure more efficiently (e.g., faster) than other surgical teams. Accordingly, the medical facility management system may recommend or give preference to scheduling the particular surgical team for the particular type of surgical procedure.

The metrics data may also be used to determine the efficiency with which medical personnel perform various tasks. For example, the metrics data may show that a particular nurse frequently views video tutorials on how to use a particular type of medical system. Accordingly, the medical facility management system may prevent the particular nurse from being assigned to medical sessions performed with the same type of medical system. Alternatively, the medical facility management system may recommend, by way of an application on the nurse's user device, certain training videos related to the same type of medical system.

The metrics data may also be used to automatically configure medical system settings. For example, the metrics data may indicate that a particular surgeon frequently adjusts ergonomic settings of a user control system (e.g., user control system 104) of a particular computer-assisted surgical system (e.g. surgical system 100). Accordingly, the medical facility management system may automatically adjust the ergonomic settings when the particular surgeon's user device detects a beacon associated with the computer-assisted surgical system.

Figure 11:
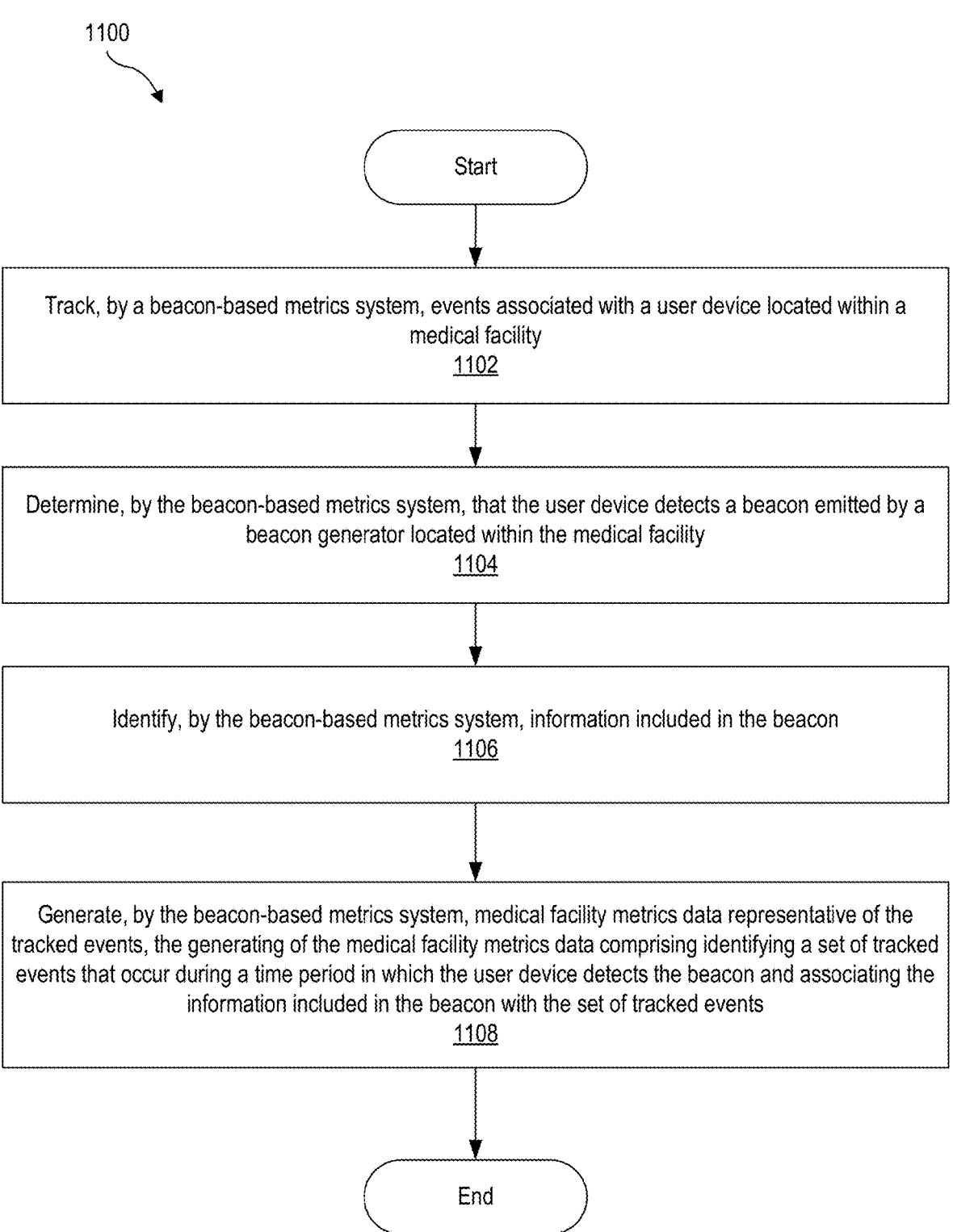
FIG. 11 illustrates an exemplary method according to principles described herein.

FIG. 11 shows an exemplary method 1100. While FIG. 11 illustrates exemplary operations according to one embodiment, other embodiments may omit, add to, reorder, combine, and/or modify any of the steps shown in FIG. 11 One or more of the operations shown in in FIG. 11 may be performed by metrics system 700, any components included therein, and/or any implementation thereof.

In operation 1102, a beacon-based metrics system tracks events associated with a user device located within a medical facility. Operation 1102 may be performed in any of the ways described herein.

In operation 1104, the beacon-based metrics system determines that the user device detects a beacon emitted by a beacon generator located within the medical facility. Operation 1104 may be performed in any of the ways described herein.

In operation 1106, the beacon-based metrics system identifies information included in the beacon. Operation 1106 may be performed in any of the ways described herein.

In operation 1108, the beacon-based metrics system generates medical facility metrics data representative of the tracked events. Operation 1108 may be performed in any of the ways described herein. For example, the beacon-based metrics system may identify a set of tracked events that occur during a time period in which the user device detects the beacon and associate the information included in the beacon with the set of tracked events.

FIG. 12 shows another exemplary method 1200 of communicatively pairing a user device with a medical system. While FIG. 12 illustrates exemplary operations according to one embodiment, other embodiments may omit, add to, reorder, combine, and/or modify any of the steps shown in FIG. 12 One or more of the operations shown in in FIG. 12 may be performed by metrics system 700, any components included therein, and/or any implementation thereof.

In operation 1202, a beacon-based metrics system determines that a user device detects a beacon emitted by a beacon generator included within a medical facility. Operation 1202 may be performed in any of the ways described herein.

In operation 1204, the beacon-based metrics system identifies information included in the beacon. Operation 1204 may be performed in any of the ways described herein.

In operation 1206, the beacon-based metrics system tracks, in response to the determination that the user device detects the beacon, events associated with the user device and that occur while the user device detects the beacon. Operation 1206 may be performed in any of the ways described herein.

In operation 1208, the beacon-based metrics system generates medical facility metrics data representative of the tracked events. Operation 1208 may be performed in any of the ways described herein. For example, the beacon-based metrics system may associate the information included in the beacon with the tracked events associated with the user device.

The foregoing configurations and embodiments have been implemented with a medical facility. In additional or alternative embodiments, the systems and methods described herein may be used to generate metrics for facilities and environments other than a medical facility, such as recreational facilities (e.g., amusement parks, sports stadiums, parks, etc.), educational facilities (e.g., schools, universities, etc.), shopping centers, business facilities (e.g., offices, research parks, etc.), laboratories, manufacturing facilities, transportation facilities (e.g., airports, train stations, etc.), and the like.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

FIG. 13 illustrates an exemplary computing device 1300 that may be specifically configured to perform one or more of the processes described herein. Any of the systems, units, computing devices, and/or other components described herein may be implemented by computing device 1300.

As shown in FIG. 13, computing device 1300 may include a communication interface 1302, a processor 1304, a storage device 1306, and an input/output ("I/O") module 1308 communicatively connected one to another via a communication infrastructure 1310. While an exemplary computing device 1300 is shown in FIG. 13, the components illustrated in FIG. 13 are not intended to be limiting. Additional or alternative components may be used in other embodiments. Components of computing device 1300 shown in FIG. 13 will now be described in additional detail.

Communication interface 1302 may be configured to communicate with one or more computing devices. Examples of communication interface 1302 include, without limitation, a wired network interface (such as a network interface card), a wireless network interface (such as a wireless network interface card), a modem, an audio/video connection, and any other suitable interface.

Processor 1304 generally represents any type or form of processing unit capable of processing data and/or interpreting, executing, and/or directing execution of one or more of the instructions, processes, and/or operations described herein. Processor 1304 may perform operations by executing computer-executable instructions 1312 (e.g., an application, software, code, and/or other executable data instance) stored in storage device 1306.

Storage device 1306 may include one or more data storage media, devices, or configurations and may employ any type, form, and combination of data storage media and/or device. For example, storage device 1306 may include, but is not limited to, any combination of the non-volatile media and/or volatile media described herein. Electronic data, including data described herein, may be temporarily and/or permanently stored in storage device 1306. For example, data representative of computer-executable instructions 1312 configured to direct processor 1304 to perform any of the operations described herein may be stored within storage device 1306. In some examples, data may be arranged in one or more databases residing within storage device 1306.

I/O module 1308 may include one or more I/O modules configured to receive user input and provide user output. I/O module 1308 may include any hardware, firmware, software, or combination thereof supportive of input and output capabilities. For example, I/O module 1308 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1308 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1308 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
a processor communicatively coupled to the memory and configured to execute the instructions to:
   track, based on medical session data logged by a computer-assisted surgical system, events associated with the computer-assisted surgical system, wherein:
      the computer-assisted surgical system includes a manipulating system and a user control system,
      the manipulating system includes a manipulator arm configured to couple with a surgical instrument, and
      the user control system controls at least one of the manipulator arm or the surgical instrument based on user input;
   determine that a user device that is not communicatively paired with the computer-assisted surgical system detects a beacon associated with the computer-assisted surgical system; and
   generate medical facility metrics data representative of the tracked events, the generating of the medical facility metrics data comprising:
      identifying a set of tracked events that occur during a time period in which the user device detects the beacon; and
      associating information associated with the user device with the set of tracked events.

2. The system of claim 1, wherein the information associated with the user device comprises at least one of an identification of the user device, an identification of a user of the user device, or a role of the user of the user device.

3. The system of claim 1, wherein the set of tracked events comprises operations of the computer-assisted surgical system performed in response to user interactions with the computer-assisted surgical system.

4. The system of claim 1, wherein the medical session data comprises kinematic data representative of a pose of the manipulator arm or the surgical instrument.

5. The system of claim 1, wherein the medical session data comprises image data representative of one or more images captured by an imaging device coupled to the computer-assisted surgical system.

6. The system of claim 1, wherein the medical session data comprises sensor data generated by one or more sensors included in or associated with the computer-assisted surgical system.

7. The system of claim 1, wherein the medical session data comprises surgical instrument data generated by the surgical instrument.

8. The system of claim 1, wherein the processor further executes the instructions to recommend, by way of an application executed by the user device and based on the medical facility metrics data, content associated with the computer-assisted surgical system.

9. The system of claim 1, wherein:
the time period in which the user device detects the beacon comprises a first medical session; and
the processor further executes the instructions to:
   determine that the user device detects the beacon during a second medical session that is different from the first medical session; and
   configure, in response to the determination that the user device detects the beacon during the second medical session, one or more settings of the computer-assisted surgical system based on the medical facility metrics data.

10. The system of claim 1, wherein:
the time period in which the user device detects the beacon comprises a first medical session; and
the processor further executes the instructions to:
   identify a user associated with the user device; and
   schedule, based on the medical facility metrics data, the user for a second medical session that is different from the first medical session.

11. The system of claim 1, wherein the beacon comprises an ultrasonic beacon.

12. A system comprising:
a memory storing instructions; and
a processor communicatively coupled to the memory and configured to execute the instructions to:
   determine that a user device detects a beacon associated with a computer-assisted surgical system, wherein:
      the computer-assisted surgical system includes a manipulating system and a user control system,
      the manipulating system includes a manipulator arm configured to couple with a surgical instrument,
      the user control system controls at least one of the manipulator arm or the surgical instrument based on user input, and
      the user device is not communicatively paired with the computer-assisted surgical system;
   track, in response to the determination that the user device detects the beacon and based on medical session data logged by the computer-assisted surgical system, events associated with the computer-assisted surgical system and that occur while the user device detects the beacon; and
   generate medical facility metrics data representative of the tracked events, the generating of the medical facility metrics data comprising associating information associated with the user device with the tracked events associated with the computer-assisted surgical system.

13. The system of claim 12, wherein the information associated with the user device comprises at least one of an identification of the user device, an identification of a user of the user device, or a role of the user of the user device.

14. The system of claim 12, wherein the tracked events comprise operations of the computer-assisted surgical system performed in response to user interactions with the computer-assisted surgical system.

15. The system of claim 12, wherein the processor further executes the instructions to recommend, by way of an application executed by the user device and based on the medical facility metrics data, content associated with the computer-assisted surgical system.

16. The system of claim 12, wherein:

the user device detects the beacon during a first medical session; and the processor further executes the instructions to:

determine that the user device detects the beacon during a second medical session that is different from the first medical session; and configure, in response to the determination that the user device detects the beacon during the second medical session, one or more settings of the computer-assisted surgical system based on the medical facility metrics data.

17. The system of claim 12, wherein:

the user device detects the beacon during a first medical session; and the processor further executes the instructions to:

identify a user associated with the user device; and schedule, based on the medical facility metrics data, the user for a second medical session that is different from the first medical session.

18. A method comprising:

tracking, by a beacon-based metrics system communicatively coupled with a computer-assisted surgical system and based on medical session data logged by the computer-assisted surgical system, events associated with the computer-assisted surgical system, wherein:

the computer-assisted surgical system includes a manipulating system and a user control system, the manipulating system includes a manipulator arm configured to couple with a surgical instrument, and the user control system controls at least one of the manipulator arm or the surgical instrument based on user input;

determining, by the beacon-based metrics system, that a user device that is not communicatively paired with the computer-assisted surgical system detects a beacon associated with the computer-assisted surgical system; and generating, by the beacon-based metrics system, medical facility metrics data representative of the tracked events, the generating of the medical facility metrics data comprising:

identifying a set of tracked events that occur during a time period in which the user device detects the beacon; and associating information associated with the user device with the set of tracked events.

19. The method of claim 18, wherein the information associated with the user device comprises at least one of an identification of the user device, an identification of a user of the user device, or a role of the user of the user device.

20. The method of claim 18, wherein the beacon comprises an ultrasonic beacon.

* * * * *